United States Patent
Wang et al.

(10) Patent No.: US 6,645,941 B1
(45) Date of Patent: Nov. 11, 2003

(54) 6,11-3C-BICYCLIC 9A-AZALIDE DERIVATIVES

(75) Inventors: Guoqiang Wang, Belmont, MA (US); Yat Sun Or, Watertown, MA (US); Ly Tam Phan, Malden, MA (US); Marina Busuyek, Natick, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/397,923

(22) Filed: Mar. 26, 2003

(51) Int. Cl.⁷ .......................... A61K 31/70; C07H 1/00; C07H 17/08
(52) U.S. Cl. .......................... 514/29; 536/7.4; 536/18.5
(58) Field of Search ................... 536/7.4, 18.5, 536/29; 514/29, 18.5

(56) References Cited

U.S. PATENT DOCUMENTS

| | | | |
|---|---|---|---|
| 4,990,602 A | 2/1991 | Morimoto et al. | 536/7.4 |
| 5,403,923 A | 4/1995 | Kashimura et al. | 536/7.4 |
| 5,444,051 A | 8/1995 | Agouridas et al. | 514/29 |
| 5,527,780 A | 6/1996 | Agouridas et al. | 514/29 |
| 5,631,355 A | 5/1997 | Asaka et al. | 536/7.4 |
| 5,686,587 A * | 11/1997 | Yang | 536/7.1 |
| 5,866,549 A | 2/1999 | Or et al. | 514/29 |
| 5,969,161 A | 10/1999 | Bonnet et al. | 549/271 |
| 6,046,171 A * | 4/2000 | Or et al. | 514/29 |
| 6,124,269 A | 9/2000 | Phan et al. | 514/29 |
| 6,399,582 B1 | 6/2002 | Hlasta et al. | 514/29 |

FOREIGN PATENT DOCUMENTS

| | | | |
|---|---|---|---|
| WO | WO 01/14397 | 3/2001 | C07H/17/08 |
| WO | WO 03/042228 | 5/2003 | C07H/17/08 |

OTHER PUBLICATIONS

Bright, et al. "Synthesis, In Vitro and In Vivo Activity of Novel 9–Deoxo–9a–Aza–9a–Homoerythromycin A Derivatives; A New Class of Macrolide Antibiotics, the Azalides"; The Journal Of Antibiotics, vol. XLI No. 8 pp. 1029–1047, 1988.

* cited by examiner

Primary Examiner—Elli Peselev
(74) Attorney, Agent, or Firm—Jason D. Ferrone

(57) ABSTRACT

The present invention discloses compounds of formula I, or pharmaceutically acceptable salts, esters, or prodrugs thereof:

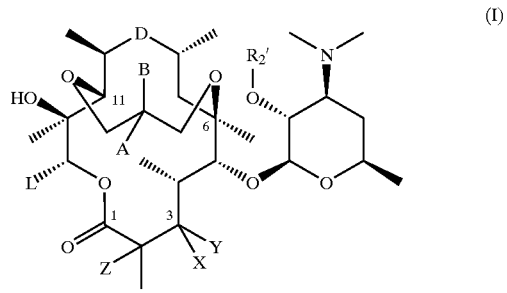

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

14 Claims, No Drawings

6,11-3C-BICYCLIC 9A-AZALIDE DERIVATIVES

TECHNICAL FIELD

The present invention relates to novel semisynthetic macrolides having antibacterial activity and useful in the treatment and prevention of bacterial infections. More particularly, the invention relates to 6,11-3C-bridged 9a-azalide derivatives, compositions comprising such compounds, methods for using the same, and processes by which to make such compounds.

BACKGROUND OF THE INVENTION

Macrolide antibacterial agents are widely used to treat and prevent bacterial infections. However, the discovery of bacterial strains which have resistance or insufficient susceptibility to macrolide antibacterial agents has promoted development of compounds with modified or improved profiles of antibiotic activity. One such class of compounds are azalides, which includes azithromycin, described in U.S. Pat. Nos. 4,474,768 and 4,517,359. Azalides are macrolide antibacterial agents with a ring structure similar to the erythronolide A or B, however azalides possess a substituted or unsubstituted nitrogen moiety at the 9a position as illustrated in the following structure:

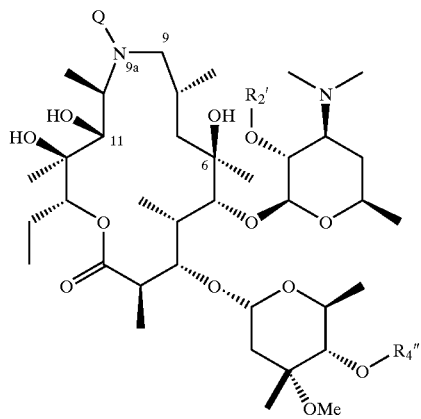

The potential for azalides to display modified or improved profiles for antibiotic activity has spawned extensive research to identify additional azalide derivatives with enhanced clinical properties. The following are examples of current efforts in azalide research:

PCT Application WO98/56801, published Dec. 17, 1998 discloses a series of 9a-(N-(alkyl))-azalide erythromycin A derivatives and a series of 9a-(N-(alkyl))-azalide 6-O-methylerythromycin A derivatives;

PCT Application WO98/56802, published Dec. 17,1998 discloses a series of 9a-(N-(H))-azalide erythromycin A derivatives and a series of 9a-(N-(H))-azalide 6-O-methylerythromycin A derivatives;

PCT Application WO99/00124, published Jan. 7, 1999 discloses a series of 9a-(N-($R_n$))-azalide 3-thioxoerythromycin A derivatives and a series of 9a-(N7($R_n$))-azalide 6-O-methyl 3-oxoerythromycin A derivatives, wherein $R_n$ is an optionally substituted alkyl or heteroalkyl;

PCT Application WO99/00125, published Jan. 7, 1999 discloses a series of 9a-(N-($R_n$))-azalide 3-oxoerythromycin A derivatives and a series of 9a-(N-($R_n$))-azalide 6-O-methyl 3-oxoerythromycin A derivatives, wherein $R_n$ is an optionally substituted alkyl or heteroalkyl; and U.S. Pat. No. 5,686,587 discloses a synthesis of azithromycin comprising introducing a 9a-(N(H))-moiety to erythromycin A by oxime formation, Beckmann rearrangement, reduction, and methylation.

SUMMARY OF THE INVENTION

The present invention provides a novel class of 6,11-3C-bridged 9a-azalide compounds, or a pharmaceutically-acceptable salt, ester, or prodrug thereof, pharmaceutical compositions comprising at least one compound of the present invention, methods of treating a bacterial infection in a subject by administering said pharmaceutical compositions, and processes of making the compounds of the present invention.

In one embodiment of the present invention there are disclosed compounds of formula I:

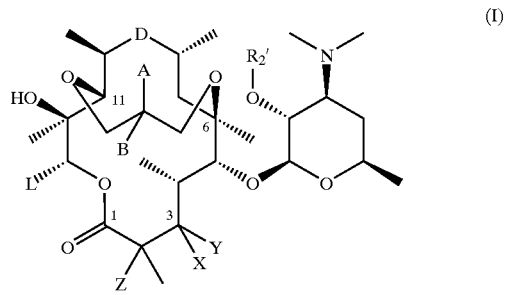

as well as the pharmaceutically acceptable salts, esters and prodrugs thereof, wherein:

A is
  i) —OH;
  ii) —$OR_p$, where $R_p$ is a hydroxy protecting group;
  iii) —$R_1$, where $R_1$ is aryl, substituted aryl, heteroaryl, or substituted heteroaryl;
  iv) —$OR_1$, where $R_1$ is as previously defined;
  v) —$R_2$, where $R_2$ is
    (a) hydrogen;
    (b) halogen;
    (c) —$C_1$–$C_6$ alkyl containing 0, 1, 2, or 3 heteroatoms selected from O, S or N, optionally substituted with one or more substituents selected from halogen, aryl, substituted aryl, heteroaryl, or substituted heteroaryl;
    (d) —$C_2$–$C_6$ alkenyl containing 0, 1, 2, or 3 heteroatoms selected from O, S, or N, optionally substituted with one or more substituents selected from halogen, aryl, substituted aryl, heteroaryl, or substituted heteroaryl; or
    (e) —$C_2$–$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
  vi) —$OR_2$, where $R_2$ is previously defined;
  vii) —$S(O)_nR_{11}$, where n=0, 1 or 2, and $R_{11}$ is $R_1$ or $R_2$, where $R_1$ and $R_2$ are as previously defined;
  viii) —$NHC(O)R_{11}$, where $R_{11}$ is as previously defined;
  ix) —$NHC(O)NHR_{11}$, where $R_{11}$ is as previously defined;

x) —NHS(O)$_2$R$_{11}$, where R$_{11}$ is as previously defined;
xi) —NR$_{14}$R$_{15}$, where R$_{14}$ and R$_{15}$ are each independently R$_{11}$, where R$_{11}$ is as previously defined; or
xii) —NHR$_3$, where R$_3$ is an amino protecting group;

B is
i) hydrogen;
ii) deuterium;
iii) halogen;
iv) —OH;
v) —R$_1$, where R$_1$ is as previously defined;
vi) —R$_2$, where R$_2$ is as previously defined; or
vii) —OR$_p$, where R$_p$ is as previously defined, provided that when B is halogen, —OH or OR$_p$, A is R$_1$ or R$_2$, where R$_1$ and R$_2$ are previously defined;

or, alternatively, A and B taken together with the carbon atom to which they are attached are
i) C=O;
ii) C(OR$_2$)$_2$, where R$_2$ is as previously defined;
iii) C(SR$_2$)$_2$, where R$_2$ is as previously defined;
iv) C[—O(CH$_2$)$_m$]$_2$, where m=2 or 3;
v) C[—S(CH$_2$)$_m$]$_2$, where m is as previously defined;
vi) C=CHR$_{11}$, where R$_{11}$ is as previously defined;
vii) C=N—O—R$_{11}$, where R$_{11}$ is as previously defined;
viii) C=NNHR$_{11}$, where R$_{11}$ is as previously defined;
ix) C=NNHC(O)R$_{11}$, where R$_{11}$ is as previously defined;
x) C=NNHC(O)NHR$_{11}$, where R$_{11}$, is as previously defined;
xi) C=NNHS(O)$_2$R$_{11}$, where R$_{11}$ is as previously defined;
xii) C=NNHR$_3$, where R$_3$ is as previously defined; or
xiii) C=NR$_{11}$, where R$_{11}$ is as previously defined;

L is
i) —CH$_3$;
ii) —CH$_2$CH$_3$;
iii) —CH(OH)CH$_3$;
iv) —C$_1$–C$_6$ alkyl, optionally substituted with one or more substituents selected from aryl, substituted aryl, heteroaryl, or substituted heteroaryl;
v) —C$_2$–C$_6$ alkenyl, optionally substituted with one or more substituents selected from aryl, substituted aryl, heteroaryl, or substituted heteroaryl; or
vi) —C$_2$–C$_6$ alkynyl, optionally substituted with one or more substituents selected from aryl, substituted aryl, heteroaryl, or substituted heteroaryl;

D is —N(Q)CH$_2$—, —N(R')C(O)—, or —N=C(OR')—, wherein R' is R$_{11}$ as previously defined;

Q is
i) hydrogen;
ii) —C$_1$–C$^{12}$-alkyl, C$_3$–C$_{12}$-alkenyl, or C$_3$–C$_{12}$-alkynyl, all optionally substituted with one, two or three substituents independently selected from:
  (a) halogen;
  (b) —OR$_6$, wherein R$_6$ is selected from:
    1. hydrogen;
    2. —C$_1$–C$_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
    3. aryl;
    4. substituted aryl;
    5. heteroaryl; and
    6. substituted heteroaryl;
  (c) —NR$_4$R$_5$, where R$_4$ and R$_5$ are each independently R$_6$, where R$_6$ is as previously defined, or in the alternative R$_4$ and R$_5$, together with the atom to which they are attached, form a heterocycloalkyl or substituted heterocycloalkyl moiety;
  (d) —N—O—R$_6$, where R$_6$ is as previously defined;
  (e) —R$_1$, where R$_1$, is as previously defined;
  (f) —C$_3$–C$_8$-cycloalkyl;
  (g) substituted —C$_3$–C$_8$-cycloalkyl;
  (h) heterocycloalkyl;
  (i) substituted heterocycloalkyl;
  (j) —NHC(O)R$_6$, where R$_6$ is as previously defined;
  (k) —NHC(O)OR$_7$, where R$_7$ is selected from:
    1. —C$_1$–C$_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
    2. aryl;
    3. substituted aryl;
    4. heteroaryl; or
    5. substituted heteroaryl;
  (l) —NHC(O)NR$_4$R$_5$, where R$_4$ and R$_5$ are as previously defined;
  (m) —OC(O)NR$_4$R$_5$, where R$_4$ and R$_5$ are as previously defined;
  (n) —OC(O)R$_7$, where R$_7$ is as previously defined;
  (o) —OC(O)OR$_7$, where R$_7$ is as previously defined;
  (p) —OC(O)NR$_4$R$_5$, where R$_4$ and R$_5$ are as previously defined,
  (q) —C(O)R$_6$, where R$_6$ is as previously defined,
  (r) —CO$_2$R$_6$, where R$_6$ is as previously defined, or
  (s) —C(O)NR$_4$R$_5$, where R$_4$ and R$_5$ are as previously defined;

X is hydrogen;
Y is
i) hydrogen;
ii) —OH;
iii) —OR$_p$, where R$_p$ is as previously defined;
iv) —OR$_{11}$, where R$_{11}$ is as previously defined;
v) —OC(O)R$_{11}$, where R$_{11}$ is as previously defined;
vi) —OC(O)NHR$_{11}$, where R$_{11}$ is as previously defined;
vii) —S(O)$_n$R$_{11}$, where n and R$_{11}$ are as previously defined;
viii) —

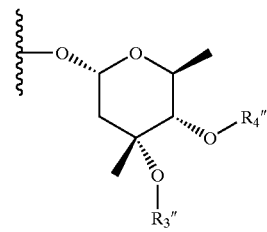

(1) where R$_3$" is hydrogen or methyl; R$_4$" is hydrogen or R$_p$, where R$_p$ is as previously defined; or
in the alternative, X and Y combined together are oxo;
Z is
i) hydrogen;
ii) methyl; or
iii) halogen; and
R$_2$' is hydrogen or R$_p$, where R$_p$, is as previously defined.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections with said pharmaceutical compositions. Suitable carriers and methods of formulation are also disclosed.

In a further aspect of the present invention there are provided processes for the preparation of 6,11-3C-bridged 9a-azalide derivatives of formula (I).

DETAILED DESCRIPTION OF THE INVENTION

A first embodiment of the present invention is a compound of formula I as illustrated above, or a pharmaceutically acceptable salt, ester or prodrug thereof.

Preferred subgenera of compounds of the present invention are:

A compound of the formula II:

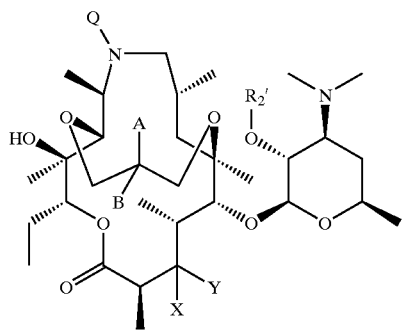

(II)

wherein A, B, Q, X, Y, and $R_2'$ are as previously defined;
A compound of formula III:

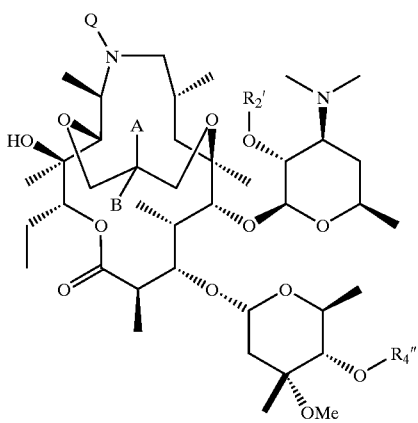

(III)

wherein A, B, Q, $R_2'$, and $R_4''$ are as previously defined;

A compound of formula IV:

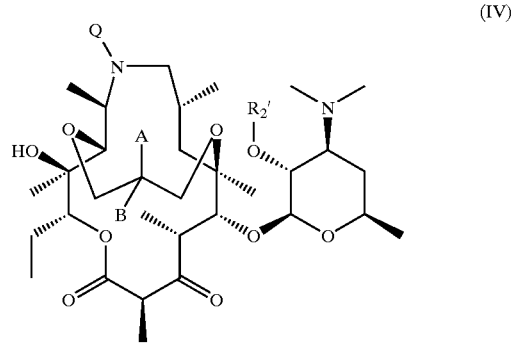

(IV)

wherein A, B, Q, and $R_2'$ are as previously defined;
A compound of formula V:

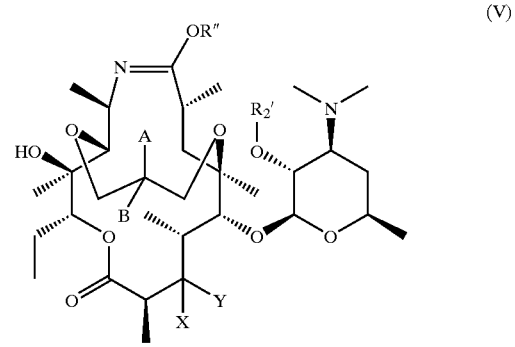

(V)

wherein A, B, Q, X, Y, R', and $R_2'$ are as previously defined; and
A compound of formula VI:

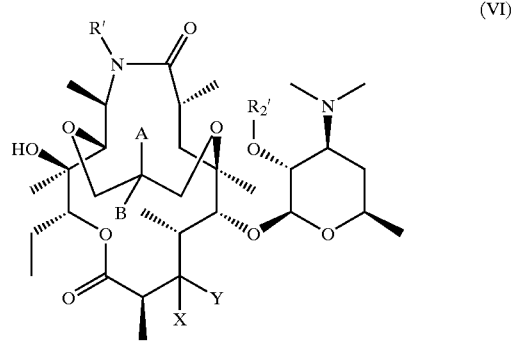

(VI)

wherein A, B, Q, X, Y, R', and $R_2'$ are as previously defined.

Representative compounds according to the invention are those selected from:

A compound of formula I, wherein A and B taken together with the carbon atom to which they are attached is C=CH$_2$, D is —N(Q)CH$_2$—, Q=X=Z=H, Y=OH, L=CH$_2$CH$_3$, $R_2'$=Ac;

A compound of formula I, wherein A and B taken together with the carbon atom to which they are attached is C=CH$_2$, D=—N(Q)CH—, Q=Z=H, X and Y taken together are oxo, L=CH$_2$CH$_3$, $R_2'$=H;

A compound of formula I, wherein A and B taken together with the carbon atom to which they are attached are

C=CH$_2$, D=—N(Q)CH$_2$—, Q=CH$_3$, X=Z=H, Y=OH, L=CH$_2$CH$_3$, R$_2$'=H;

A compound of formula I, wherein A and B taken together with the carbon atom to which they are attached are C=CH$_2$, D=—N(Q)CH$_2$—, Q=CH$_3$, Z=H, X and Y taken together are oxo, L=CH$_2$CH$_3$, R$_2$'=H;

A compound of formula I, wherein A=H, B=CH$_3$, D=—N(Q)CH$_2$—, Q=X=Z=H, Y=OH, L=CH$_2$CH$_3$, R$_2$'=Ac;

A compound of formula I, wherein A=H, B=CH$_3$, D=—N(Q)CH$_2$—, Q=X=Z=H, Y=OH, L=CH$_2$CH$_3$, R$_2$'=H;

A compound of formula I, wherein A=H, B=CH$_3$, D=—N(Q)CH—, Q=Z=H, X and Y taken together are oxo, L=CH$_2$CH$_3$, R$_2$'=H;

A compound of formula I, wherein A=H, B=CH$_3$, D=—N(Q)CH$_2$—, Q=CH$_3$, X=Z=H, Y=OH, L=CH$_2$CH$_3$, R$_2$'=H;

A compound of formula I, wherein A=H, B=CH$_3$, D=—N(Q)CH—, Q=CH$_3$, Z=H, X and Y taken together are oxo, L=CH$_2$CH$_3$, R$_2$∝=H;

A compound of formula I, wherein A=H, B=CH$_3$, D=—(C=NOH)—, X=Z=

H, Y =

L=CH$_2$CH$_3$, R$_2$'=Ac;

A compound of formula I, wherein A=H, B=CH$_3$, D=—NH(C=O)—, X=Z=

H, Y =

L=CH$_2$CH$_3$, R$_2$'=Ac;

A compound of formula I, wherein A=H, B=CH$_3$, D=—NH(C=O)—, X=Z=

H, Y =

L=CH$_2$CH$_3$, R$_2$'=H;

A compound of formula I, wherein A and B taken together with the carbon atom to which they are attached =C=CH$_2$, D=—N(Q)CH—, Q=CH$_2$Ph, Z=X=H, Y=OH, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$Ph, Z=H, X and Y are taken together are oxo, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$(2-pyridyl), Z=X=H, Y=OH, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$(2-pyridyl), Z=H, X and Y taken together are oxo, L=CH$_2$CH$_3$, R$_2$'=H;

A compound of formula I, wherein A and B taken together with the carbon atom to,which they are attached C=CH$_2$, D=—N(Q)CH$_2$—, Q=CH$_2$(3-quinolyl), Z=H, X and Y taken together are oxo, L=CH$_2$CH$_3$, R$_2$'=H;

A compound of formula I, wherein A and B taken together with the; carbon atom to which they are attached =C=CH$_2$, D=—N(Q)CH$_2$—, Q=CH$_2$(3-quinolyl), Z=H, X and Y taken together are oxo, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$(CH=CH)Ph, Z=X=H, Y=OH, L=CH$_2$CH$_3$, R$_2$'=H;

A compound of formula I, wherein A and B taken together with the carbon atom to which they are attached =C=CH$_2$, D=—N(Q)CH—, Q=CH$_2$(CH=CH)Ph, Z=H, X and Y taken together are oxo, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$CH=CH(2-pyridyl), Z=X=H, Y=OH, L=CH$_2$CH$_3$, R$_2$'=H;

A compound of formula I, wherein A and B taken together with the carbon atom to which they are attached =C=CH$_2$, D=—N(Q)CH—, Q=CH$_2$CH=CH(2-pyridyl), Z=H, X and Y taken together are oxo, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$C≡C(3-quinolyl), Z=H, X and Y taken together are oxo, L=CH$_2$CH$_3$, R$_2$'=H;

A compound of formula I, wherein A and B taken together with the carbon atom to which they are attached =C=CH$_2$, D=—N(Q)CH$_2$—, Q=CH$_2$C≡C(3-quinolyl), Z=H, X and Y taken together are oxo, L=CH$_2$CH$_3$, R$_2$'=H;

A compound of formula I, wherein A and B taken together with the carbon atom to which they are attached =C=CH—CH=CHPh, D=—N(Q)CH$_2$—, Q=CH$_3$, Z=H, X and Y taken together are oxo, L=CH$_2$CH$_3$, R$_2$'=H;

A compound of formula I, wherein A and B taken together with the carbon atom to which they are attached =C=CH—CH=CH(3-pyridyl), D=—N(Q)CH$_2$—, Q=CH$_3$, Z=H, X and Y taken together are oxo, L=CH$_2$CH$_3$, R$_2$'=H;

A compound of formula I, wherein A and B taken together with the carbon atom to which they are attached =C=CH—CH=CH(3-quinolyl), D=—N(Q)CH$_2$—, Q=CH$_3$, Z=H, X and Y taken together are oxo, L=CH$_2$CH$_3$, R$_2$'=H;

A compound of formula I, wherein A and B taken together with the carbon atom to which they are attached =C=CH-3-quinolyl, D=—N(Q)CH$_2$—, Q=CH$_3$, Z=H, X and Y taken together are oxo, L=CH$_2$CH$_3$, R$_2$'=H; or A compound of formula I, wherein A and B taken together with the carbon atom to which they are attached =C=CH—Ph, D=—N(Q)CH—, Q=CH$_3$, Z=H, X and Y taken together are oxo, L=CH$_2$CH$_3$, R$_2$'=H.

Another embodiment of the present invention is a process by which to make compounds of formula I as previously described.

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art, or a pharmaceutically acceptable salt, ester, or prodrug thereof, with a pharmaceutically acceptable carrier or excipient.

Definitions

The terms "C$_1$–C$_3$ alkyl," "C$_1$–C$_6$ alkyl" or "C$_1$–C$_{12}$ alkyl," as used herein, refer to saturated, straight- or branched-chain hydrocarbon radicals containing between one and three, one and twelve, or one and six carbon atoms, respectively. Examples of C$_1$–C$_3$ alkyl radicals include methyl, ethyl, propyl and isopropyl radicals; examples of C$_1$–C$_6$ alkyl radicals include, but are not limited to, methyl, ethyl, propyl, isopropyl, n-butyl, tert-butyl, neopentyl and n-hexyl radicals; and examples of C$_1$–C$_{12}$ alkyl radicals include, but are not limited to, ethyl, propyl, isopropyl, n-hexyl, octyl, decyl, dodecyl radicals.

The terms "C$_2$–C$_{12}$ alkenyl" or "C$_2$–C$_6$ alkenyl," as used herein, denote a monovalent group derived from a hydrocarbon moiety containing from two to twelve or two to six carbon atoms having at least one carbon—carbon double bond by the removal of a single hydrogen atom. Alkenyl groups include, but are not limited to, for example, ethenyl, propenyl, butenyl, 1-methyl-2-buten-1-yl, and the like.

The terms "C$_2$–C$_{12}$ alkynyl" or "C$_2$–C$_6$ alkynyl," as used herein, denote a monovalent group derived from a hydrocarbon moiety containing from two to twelve or two to six carbon atoms having at least one carbon—carbon triple bond by the removal of two hydrogen atoms. Representative alkynyl groups include, but are not limited to, for example, ethynyl, 1-propynyl, 1-butynyl, and the like.

The terms "halo" and "halogen," as used herein, refer to an atom selected from fluorine, chlorine, bromine and iodine.

The term "haloalkyl" denotes an alkyl group, as defined above, having one, two or three halogen atoms attached thereto, and is exemplified by such groups as chloromethyl, bromoethyl, trifluoromethyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like. Aryl groups (including bicyclic aryl groups) can be unsubstituted or substituted with one, two or three substituents independently selected from lower alkyl, substituted lower alkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "substituted aryl," as used herein, refers to an aryl group, as defined herein, substituted by independent replacement of one, two or three of the hydrogen atoms thereon with F, Cl, Br, I, OH, NO$_2$, CN, C(O)—C$_1$–C$_6$-alkyl, C(O)-aryl, C(O)-heteroaryl, CO$_2$-alkyl, CO$_2$-aryl, CO$_2$-heteroaryl, CONH$_2$, CONH—C$_1$–C$_6$-alkyl, CONH-aryl, CONH-heteroaryl, OC(O)—C$_1$–C$_6$-alkyl, OC(O)-aryl, OC(O)-heteroaryl, OCO$_2$-alkyl, OCO$_2$-aryl, OCO$_2$-heteroaryl, OCONH$_2$, OCONH—C$_1$–C$_6$-alkyl, OCONH-aryl, OCONH-heteroaryl, NHC(O)—C$_1$–C$_6$-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C$_1$–C$_6$-alkyl, NHCONH-aryl, NHCONH-heteroaryl, SO$_2$–C$_1$–C$_6$-alkyl, SO$_2$-aryl, SO$_2$-heteroaryl, SO$_2$NH$_2$, SO$_2$NH—C$_1$–C$_6$-alkyl, SO$_2$NH-aryl, SO$_2$NH-heteroaryl, C$_1$–C$_6$-alkyl, C$_3$–C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C$_1$–C$_6$-alkoxy, methoxymethoxy, methoxyethoxy, amino, benzylamino, arylamino, heteroarylamrino, C$_1$–C$_3$-alkylamino, thio, aryl-thio, heteroarylthio, benzyl-thio, C$_1$–C$_6$-alkyl-thio, or methylthiomethyl.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, two or three of the hydrogen atoms thereon with F, Cl, Br, I, OH, NO$_2$, CN, C(O)—C$_1$–C$_6$-alkyl, C(O)-aryl, C(O)-heteroaryl, CO$_2$-alkyl, CO$_2$-aryl, CO$_2$-heteroaryl, CONH$_2$, CONH—C$_1$–C$_6$-alkyl, CONH-aryl, CONH-heteroaryl, OC(O)—C$_1$–C$_6$-alkyl, OC(O)-aryl, OC(O)-heteroaryl, OCO$_2$-alkyl, OCO$_2$-aryl, OCO$_2$-heteroaryl, OCONH$_2$, OCONH—C$_1$–C$_6$-alkyl, OCONH-aryl, OCONH-heteroaryl, NHC(O)—C$_1$–C$_6$-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C$_1$–C$_6$-alkyl, NHCONH-aryl, NHCONH-heteroaryl, SO$_2$–C$_1$–C$_6$-alkyl, SO$_2$-aryl, SO$_2$-heteroaryl, SO$_2$NH$_2$, SO$_2$NH—C$_1$–C$_6$-alkyl, SO$_2$NH-aryl, SO$_2$NH-heteroaryl, C$_1$–C$_6$-alkyl, C$_3$–C$_6$-cycloalkyl, CF$_3$, CH$_2$CF$_3$, CHCl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C$_1$–C$_6$-alkoxy, methoxymethoxy, methoxyethoxy, amino, benzylamino, arylamino, heteroarylamino, C$_1$–C$_3$-alkyl-amino, thio, aryl-thio, heteroarylthio, benzyl-thio, C$_1$–C$_6$-alkyl-thio, or methylthiomethyl.

The term "C$_3$–C$_{12}$-cycloalkyl" denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl.

The term "substituted C$_3$–C$_{12}$-cycloalkyl," as used herein, refers to a C$_3$–C$_{12}$-cycloalkyl group as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$–$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, arylthio, heteroarylthio, benzyl-thio, $C_1$–$C_6$-alkyl-thio, or methylthiomethyl.

The term "heterocycloalkyl," as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be-quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$–$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, arylthio, heteroarylthio, benzyl-thio, $C_1$–$C_6$-alkyl-thio, or methylthiomethyl.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to, methylamino, dimethylamino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylarnino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl)($C_1$–$C_{12}$ alkyl).

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-dimethylsilyl, tert-butyidiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N.Y., 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain two or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

As used herein, unless otherwise indicated, the term "bacterial infection(s)" or "protozoa infections"; includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or Peptostreptococcus spp.; *pharynigitis*, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus*, coagulase-positive *staphylococci* (i.e., *S. epidermidis, S. hemolyticus*, etc.), *Streptococcus pyogenes, Streptococcus agalactiae, Streptococcal groups C-F* (minute-colony streptococci), viridans streptococci, *Corynebacterium minutissimum*, Clostridium spp., or *Bartonella henselae*; uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neserria gonorrheae*; toxin diseases related to infection by *S. aureus* (food poisoning and Toxic shock syndrome), or Groups A, S. and *C streptococci*; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated Mycobacterium avium complex (MAC) disease related to infection by Mycobacterium avium, or *Mycobacterium intracellulare*; gastroenteritis related to infection by *Campylobacter jejuni*; intestinal protozoa related to infection by Cryptosporidium spp. odontogenic infection related to infection by viridans streptococci; persistent cough related to infection by *Bordetella pertussis*; gas gangrene related to infectionpby *Clostridium perfringens* or Bacteroides spp.; and atherosclerosis related to infection by *Helicobacter pylori* or *Chlamydia pneumoniae.*

Bacterial infections and protozoa infections and disorders related to such infections that may be treated or prevented in animals include the following: bovine respiratory disease related to infection by *P. haem., P. multocida, Mycoplasma bovis,* or Bordetella spp.; cow enteric disease related to infection by *E. coli* or protozoa (i.e., coccidia, cryptosporidia, etc.), dairy cow mastitis related to infection by *Staph. aureus, Strep. uberis, Strep. agalactiae, Step. dysgalactiae,* Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae*; cow footrot related to infection by Fusobacterium spp.; cow metritis related to infection by *E. coli*; cow hairy warts related to Infection by Fusobacterium necrophorum or Bacteroides nodosus; cow pink-eye related to infection by *Moraxella bovis*, cow prernature abortion related to infection by protozoa (i.e. neosporium); urinary tract infection in dogs and cats related to infection by *E. coli*; skin and soft tissue infections in dogs and cats related to infection by Staph. epidermidis, Staph. interrmedius, coagulase neg. Staph. or *P. multocida*; and dental or mouth infections in dogs and oats related to infection by Alcaligenes spp., Bacteroides spp., Clostridium spp., Enterobacter spp., Eubacterium, Peptostreptococcus, Porphfyromonas, or Prevotella. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in bMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5\times10^5$ CFU/mL by optical comparison to a 0.5 McFarland turbidity standard. The plates were inoculated with 10 $\mu$l/well of adjusted bacterial inoculum. The 96 well plates were covered and incubated at 35+/$-2°$ C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the ranrge from about 64 µg/ml to about 0.03 µg/ml.

All in vitro testing follows the guidelines described in the Approved Standards M7-A4 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline;. Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, iritrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamidej oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage. ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which appear in the following synthetic schemes and examples are:

Ac for acetyl;
AIBN for azobisisobutyronitrile;
Boc for tert-butoxycarbonyl;
Bu$_3$SnH for tributyltin hydride;
Bz for benzyl;
CDI for carbonyldiimidazole;
dba for dibenzylidene acetone;
DBU for 1,8-diazabicyclo[5.4.0]undec-7-ene;
DEAD for diethylazodicarboxylate;
Dess-Martin periodinane for 1,1,1-tris(acetyloxy)-1,1-dihydro-1,2-benziodoxol-3-(1H)-one;
DMAP for dimethylaminopyridine;
DMF for dimethyl formamide;
DMSO for dimethyl sulfoxide;
DPPA for diphenylphosphoryl azide;
dppb for diphenylphosphino butane;
EtOAc for ethyl acetate;
iPrOH for isopropanol;
NaHMDS for sodium bis(trimethylsilyl)amide;
NMO for N-methylmorpholine N-oxide;
MeOH for methanol;
MOM for methoxymethyl;
PDC for pyridinium dichromate;
Ph for phenyl;
POPd for dihydrogen dichlorobis(di-tert-butylphosphinito-κP)palladate(II);
TBAHS for tetrabutyl ammonium hydrogen sulfate;
TBS for tert-butyl dimethylsilyl;
TEA for triethylamine;
THF for tetrahydrofuran;
TMS for trimethyl silyl;
TPAP for tetra-n-propyl ammonium perruthenate;
TPP for triphenylphosphine; and
Tris for Tris(hydroxymethyl)aminomethane.

Synthetic Methods

The compounds and processes of the present invention will be better understood in connection with the following synthetic schemes that illustrate the methods by which the compounds of the invention may be prepared.

A preferred intermediate for the preparation of compounds. represented by formula I is a compound represented by the formula Ia:

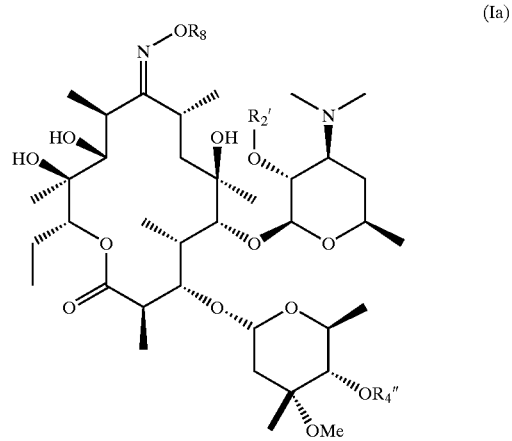

(Ia)

wherein

1) $R^8$ is
   a. hydrogen,
   b. —CH$_2$O(CH$_2$)$_2$OCH$_3$,
   c. —CH$_2$O(CH$_2$O)$_n$CH$_3$ where n is as previously defined;
   d. —C$_1$–C$_{12}$ alkyl, optionally substituted with one or more substituents selected from aryl, substituted aryl, heteroaryl and substituted heteroaryl;
   e. —C$_3$–Cl$_2$ cycloalkyl;
   f. —C(O)—C$_1$–C$_{12}$ alkyl;
   g. —C(O)—C$_3$–C$_{12}$ cycloalkyl;
   h. —C(O)—R$_1$, where R$_1$ is as previously defined; or
   i. —Si(R$_a$)(R$_b$)(R$_c$), wherein R$_a$, R$_b$ and R$_c$ are each independently selected from C$_1$–C$_{12}$ alkyl, aryl and substituted aryl; and 2) R$_2$' and R$_4$" are as previously defined.

A second preferred intermediate for the preparation of compounds represented by formula I is a compound represented by the formula Ib

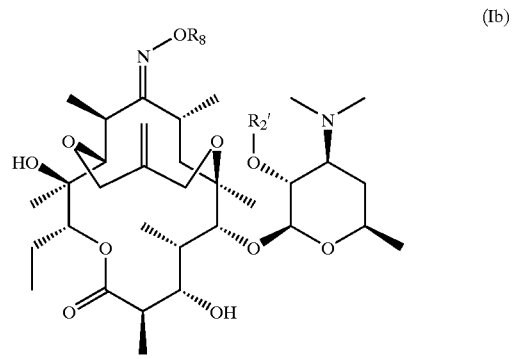

(Ib)

wherein R$_2$' is as previously defined.

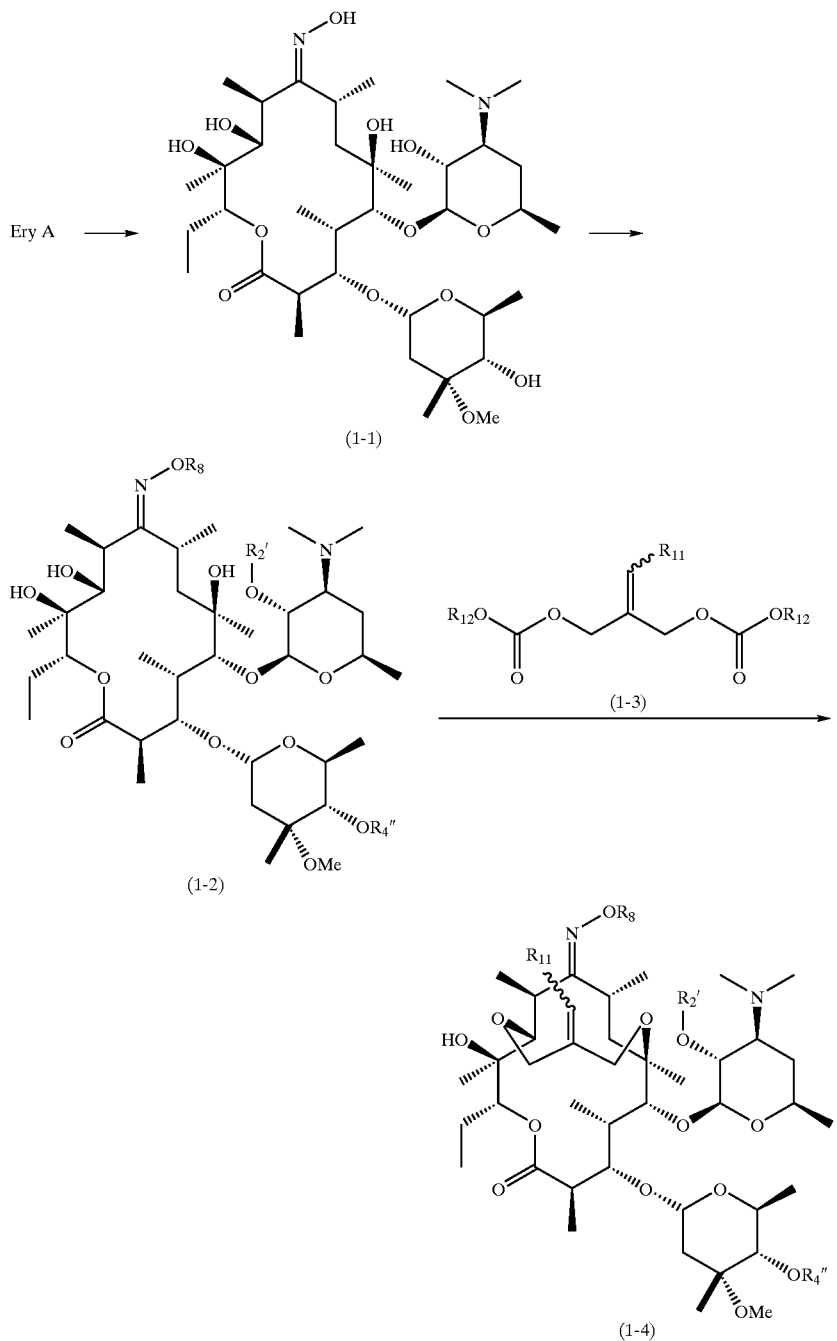

Scheme 1

A process of the invention, as illustrated in Scheme 1, involves preparing a compound of formula (1-4) by reacting a compound of formula (1-2) with a suitable alkylating agent.

In accordance with Scheme 1, the 9-keto group of erythromycins can be initially converted into an oxime by methods described in U.S. Pat. No. 4,990,602, followed by the protection of the 2'- and 4"-hydroxyl and, if desired, the oxime groups of the erythromycin derivatives to obtain the compounds of formula (1-2).

The preparation of protected erythromycins is also described in U.S. Pat. Nos. 4,990,602; 4,331,803; 4,680,386; 4,670,549, European Patent Application No. EP 260,938.

The 2'- and 4"-hydroxyl groups are protected by reaction with suitable hydroxyl protecting reagents in an aprotic solvent. Typical hydroxyl protecting reagents include, but are not limited to, acetylating agents, silylating agents, acid anhydrides, and the like. Examples of hydroxyl protecting reagents are, for example, acetyl chloride, acetic anhydride, benzoyl chloride, benzoic anhydride, benzyl chloroformate, hexamethyldisilazane, and trialkylsilyl chlorides.

Examples of aprotic solvents are dichloromethane, chloroform, tetrahydrofuran, N-methylpyrrolidinone, dimethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methylpyrrolidinone or mixtures thereof. A more thorough discussion of solvents and conditions for protecting the hydroxyl group can be found in T. W. Greene and P. G. M. Wuts, *Protective Groups in Organic Synthesis*, $3^{rd}$ ed., John Wiley & Son, Inc, 1999.

Protection of 2'- and 4''-hydroxyl groups may be accomplished sequentially or simultaneously to provide compound (1-2) where $R_2'$ and/or $R_4''$ can be, for example, acetyl, benzoyl, trimethylsilyl, and the like. Preferred protecting groups include acetyl, benzoyl, and trimethylsilyl. A particularly preferred group for protecting the hydroxyl and oxime groups is the acetyl protecting group, wherein $R_2'=R_4''=R_6=Ac$.

Acetylation of the hydroxyl group is typically accomplished by treating the compound (1-1) with an acetylating reagent, for example, acetic anhydride or acetyl chloride.

The erythromycin derivative of formula (1-2) is then reacted with an alkylating agent of the formula:

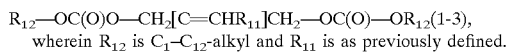

wherein $R_{12}$ is $C_1$-$C_{12}$-alkyl and $R_{11}$ is as previously defined.

Most palladium (O) catalysts are expected to work in this process. Some palladium (II) catalysts, such as palladium (II) acetate, which is converted into a palladium (O) species in-situ by the actions of a phosphine, will work as well. See, for example, Beller et al. *Angew. Chem. Int. Ed. Engl.*, 1995, 34 (17), 1848. The palladium catalyst can be selected from, but not limited to, palladium (II) acetate, tetrakis(triphenylphospine)palladium (O), tris(dibenzylideneacetone)dipalladium, tetradibenzylideneacetone)dipalladium and the like. Palladium on carbon and palladium (II) halide catalysts are less preferred than other palladium catalysts for this process. Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri-o-tolyl-phosphine, and the like. The reaction is carried out in an aprotic solvent, preferably at elevated temperature, preferably at or above 50° C. Suitable aprotic solvents include, but are not limited to, tetrahydrofuran, N,N-dimethylformamide, dirnethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene.

Generally, the alkylating agents have the formula (1-3) as previously described. The preferred alkylating agents are those wherein $R_{12}$ is tert-butyl, isopropyl or isobutyl. The alkylating reagents are prepared by reaction of a diol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about −30° C. to approximately 30° C. Preferably the alkylating reagent is di-tert-butyl dicarbonate.

An alternative method of converting the alcohol into the carbonate involves treating the alcohol with phosgene or triphosgene to prepare the chloroformate derivative of the diol. The di-chloroformate derivative is then converted into the di-carbonate by the methods described in Cotarca, L., Delogu, P., Nardelli, A., Sunijic, V, *Synthesis*, 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate, DMAP, pyridine, triethylamine and the like. The temperature can vary from 0° C. to approximately 60° C. The reaction runs to completion in 3 to 5 hours.

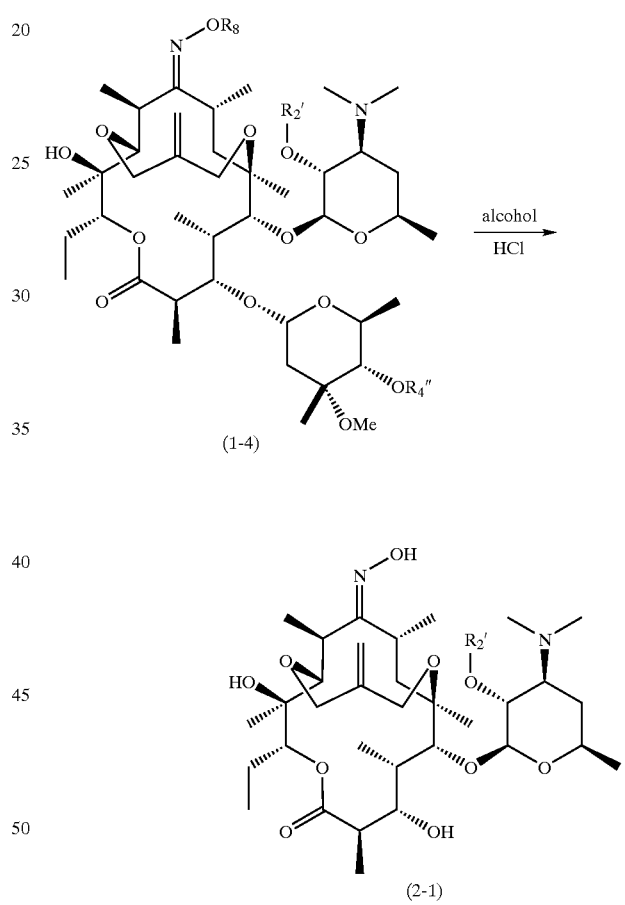

Another process of the invention involves the removal of the cladinose moiety of the compounds of formula I. The cladinose moiety of the macrolide compound (1-4) is removed either by mild acid hydrolysis or by enzymatic hydrolysis to afford compounds of formula (2-1) in Scheme 2. Representative acids include, but are not limited to, dilute hydrochloric acid, sulfuric acid, perchloric acid, chloroacetic acid, dichloroacetic acid or trifluoroacetic acid. Suitable solvents for the reaction include, but are not limited to, methanol, ethanol, isopropanol, butanol, water and mixtures there of. Reaction times are typically 0.5 to 24 hours. The reaction temperature is preferably 0 to 80° C.

Scheme 3

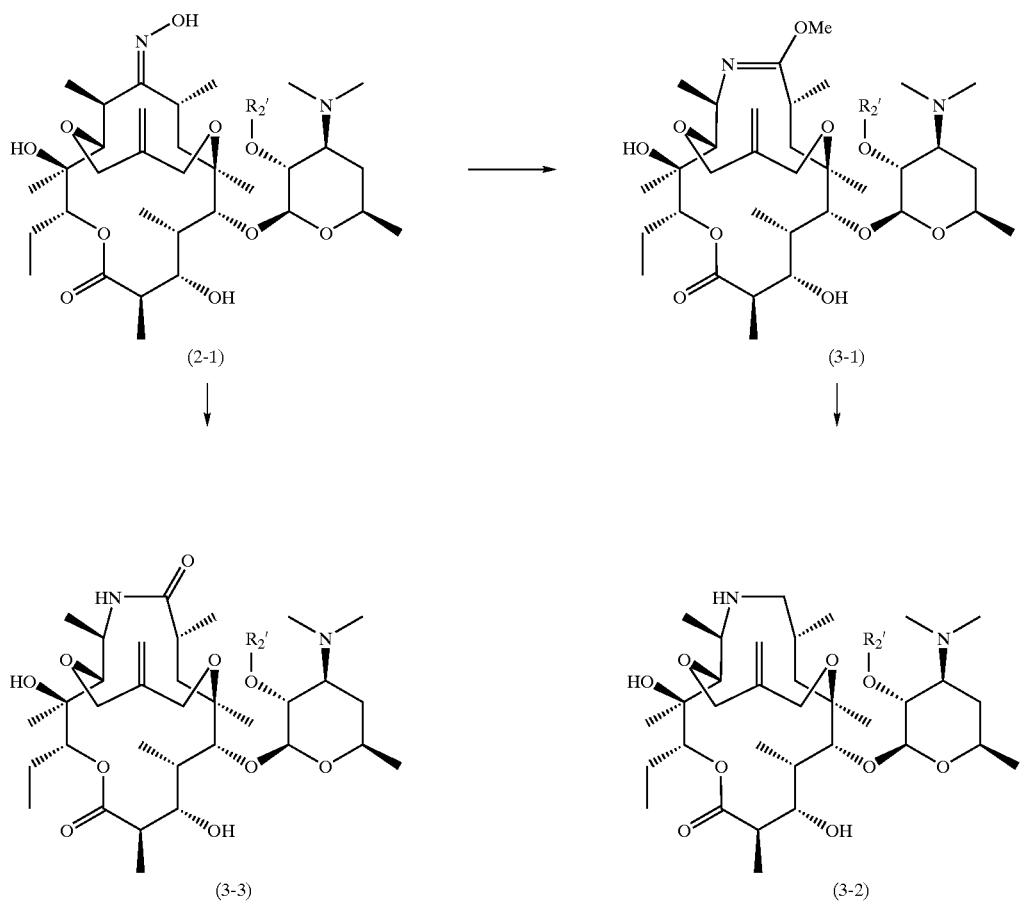

The compound of formula (2-1) where $R_2'$ is Ac can be converted into the compound of formula (3-1) and (3-3) by Beckmann rearrangement. Thus, the compound of formula (2-1) is treated with oxime activating agents and subsequently quenched by addition of methanol to provide the compounds of formula (3-1). Representative oxime activating agents include, but are not limited to, sulfonic anhydrides and sulfonyl halides such as p-toluenesulfonic anhydride, methanesulfonic anhydride, p-toluenesulfonyl chloride, methanesulfonyl chloride, p-bromosulfonyl chloride, optionally in the presence of a base such as, but not limited to, pyridine, triethyl amine, diisopropylethyl amine, $NaHCO_3$, $Na_2CO_3$, $KHCO_3$ and $K_2CO_3$. For further details concerning the Beckmann rearrangement see L. G. Donaruma, W. Z. Heldt, Org. React. 11, 1–156 (1960); R. E. Gawley, ibid. 35, 1–420 (1988); C. G. McCarty in The Chemistry of the Carbon-Nitrogen Double Bond, S. Patai, Ed. (Interscience, New York, 1970) pp 408–439; J. R. Hauske, Comp. Org. Syn. 1, 98–100 (1991); K. Maruoka, H. Yamamoto, ibid. 6, 763–775; D. Craig, ibid. 7, 689–702.

Reduction of compounds of formula (3-1) to compounds of formula (3-2) can be achieved by treatment of the former with reducing agents including, but not limited to, borane in THF, borane dimethylsulfide, sodium cyanoborohydride, sodium borohydride optionally in the presence of an acid such as $TiCl_4$, $COCl_2$, $AlCl_3$, methanesulfonic acid, or acetic acid. Solvents which are applicable include, but are not limited to, tetrahydrofuran, 1,4-dioxane, 1,2-dimethoxyethane, isopropanol, ethanol, butanol acetonitrile, diethyl ether, dichloromethane, water and mixtures thereof. The reaction temperature is −78° C. to 30° C. In a particularly preferred embodiment, compounds of formula (2-1) are treated with p-toluenesulfonic anhydride and triethylamine in methylene chloride and subsequently quenched with methanol to provide compounds of formula (3-1). Compounds of formula (3-1) are then treated with $NaBH_4$ in methanol to provide the compounds of formula (3-2). The compounds of formula (3-3) were synthesized via treatment of compounds of formula (2-1) with p-toluenesulfonyl chloride and $NaHCO_3$ in acetone and water.

Scheme 4

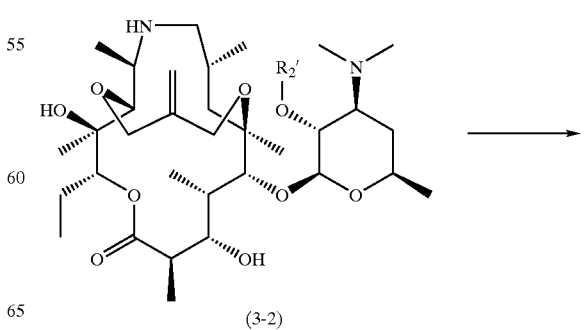

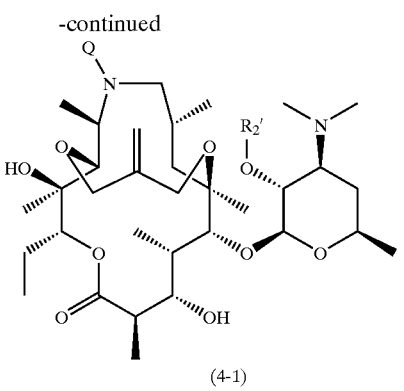

(4-1)

Compounds of formula (3-2) can be converted to compounds of formula (4-1) by treatment of the former with alkylating agent Q—$X_1$, wherein $X_1$ is a halo leaving group, in the presence of base. An alternative means of converting cormpounds of formula (3-2) to compounds of formula (4-1) is treatment of the compounds of formula (3-2) with an aldehyde Q—CHO in the presence of acetic acid and excess $NaCNBH_3$ to provide compounds of formula (4-1) where Q is —$CH_2R_2$, wherein $R_2$ is as previously defined. Examples of solvents include, but are not limited to, acetonitrile, diethylether, dichloromethane, chloroform, ethyl acetate, THF, dioxane or mixtures thereof. The reaction generally proceeds at from −20° C. to 80° C. for 30 minutes to 18 hours. In a particularly preferred-embodiment, Q—CHO is reacted with (3-2) in chloroform at 80° C.

Scheme 5

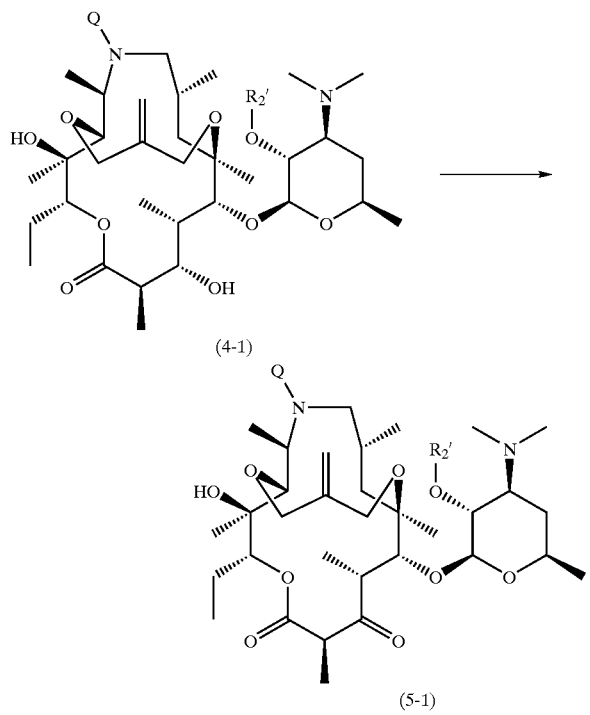

Conversion of compounds of formula (4-1) to compounds of formula (5-1) can be accomplished by oxidation of the 3-hydroxy group to a 3-oxo group using Dess-Martin perio dinane (for further details concerning the Dess-Martin oxidation see D. B. Dess, J. C. Martin, *J. Org. Chem.* 48, 4155 (1983)), a Corey-Kim reaction with N-chlorosuccinimide-dimethylsulfide (for further details concerning the Corey-Kim oxidation reaction see E. J. Corey, C. U. Kim, *J. Am. Chem. Soc.* 94, 7586 (1972)), or a Moffat oxidation with a carbodiimide-DMSO complex in the presence of pyridinium trifluoroacetate, TPAP, PDC, and the like (for further details concerning the Moffat oxidation see J. G. Moffatt, "Sulfoxide-Carbodiimide and Related Oxidations" in *Oxidation* vol. 2, R. L. Augustine, D. J. Trecker, Eds. (Dekker, New York, 1971) pp 1–64; T. T. Tidwell, *Org. React.* 39, 297–572 passim (1990); and T. V. Lee, *Comp. Org. Syn.* 7, 291–303 passim (1991)). In a preferred embodiment, compounds of formula (4-1) are treated with Dess-Martin periodinane in dichloromethane at about 0° C. to about 25° C. for approximately 0.5 to 4 hours to produce compounds of formula (5-1).

Scheme 6

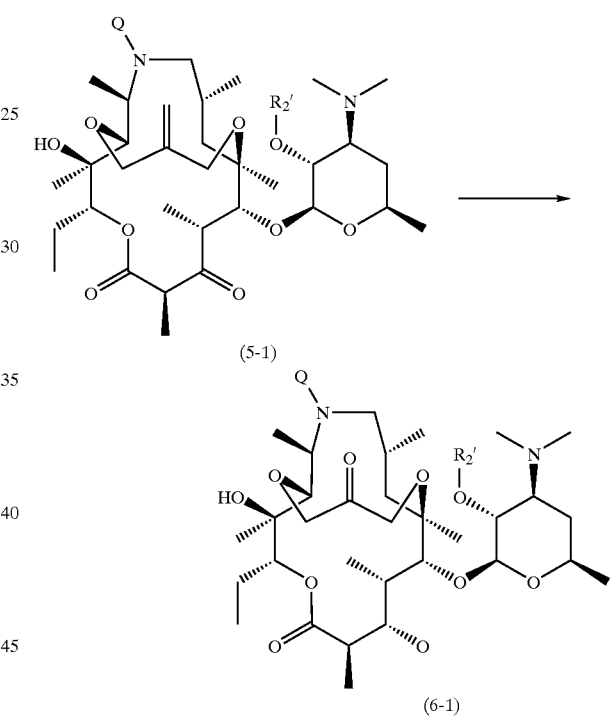

Scheme 6 illustrates another process of the invention by which to prepare compound of the present invention. Conversion of alkenes (5-1) into ketones (6-1) can be accomplished by ozonolysis followed by decomposition of the ozonide with the appropriate reducing agents. The reaction is typically carried out in an inert solvent such as, but not limited to, methanol, ethanol, ethyl acetate, glacial acetic acid, chloroform, methylene chloride or hexane or mixtures thereof, preferably methanol, preferably at −78° C. to −20° C. Representative reducing agents are, for example, triphenylphosphine, trimethylphosphite, thiourea, and dimethyl sulfide, preferably triphenylphosphine. A more thorough discussion of ozonolysis and conditions therefor may be found in J. March, *Advanced Organic Chemistry*, 4th ed., Wiley & Son, Inc, 1992. Alternatively, compounds of formula (6-1) can be prepared from compounds of formula (5-1) dihydroxydation with $OSO_4$ followed by $NaIO_4$ cleavage to provide the compounds of formula of (6-1).

Scheme 7

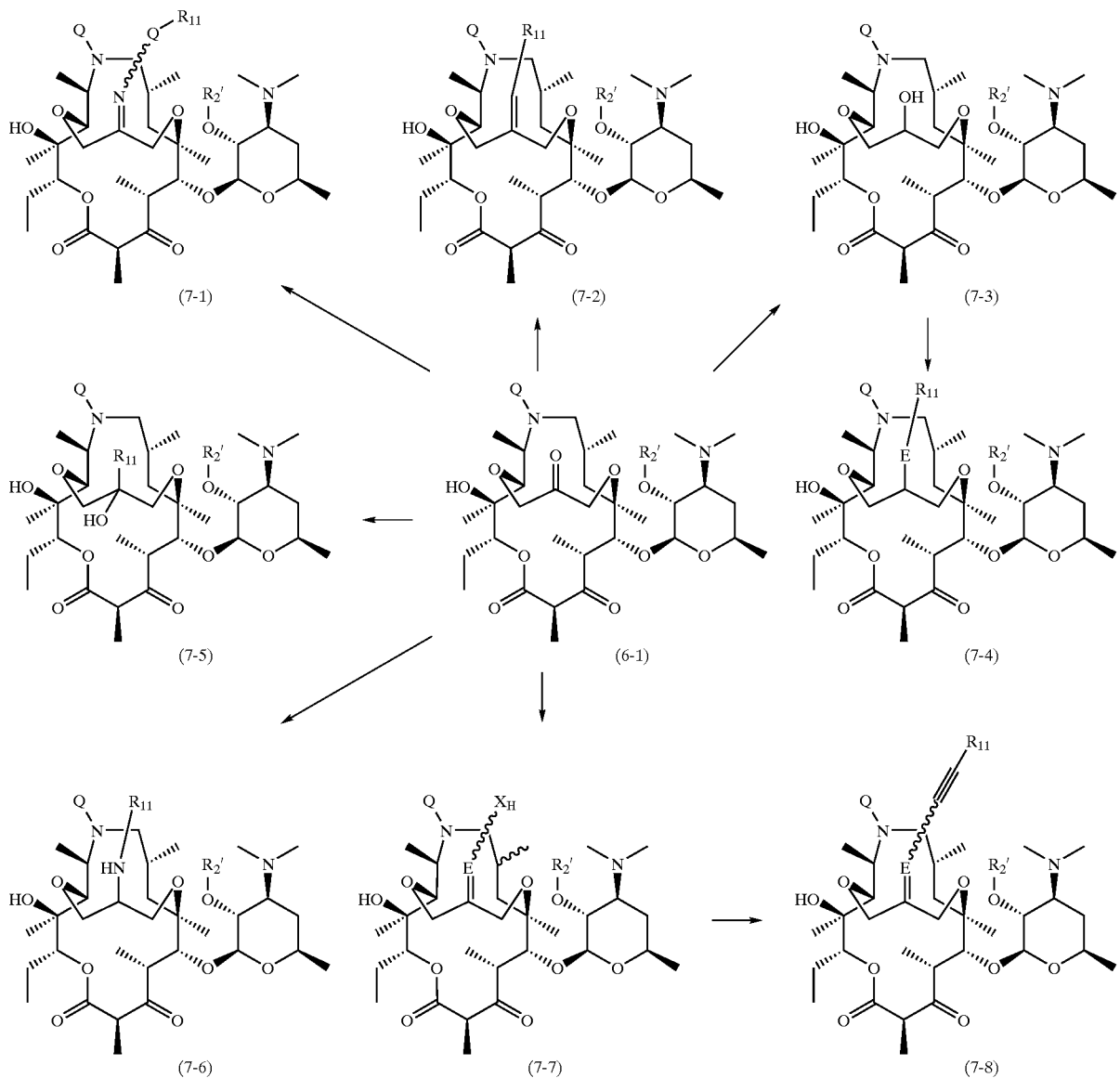

Compounds according to the invention of the formula (6-1) can be further functionalized in a variety of ways. Scheme 7 details a procedure for the conversion of the ketone of formula (6-1) into an oxime of formula (7-1). Oxime formation can be accomplished using the appropriate substituted hydroxylamine under either acidic or basic conditions in a variety of solvents. Representative acids include, but are not limited to, hydrochloric, phosphoric, sulfuric, p-toluenesulfonic, and pyridinium p-toluene sulfonate. Likewise, representative bases include, but are not limited to, triethylamine, pyridine, duisopropylethyl amine, 2,6-lutidine, and the like. Appropriate solvents include, but are not limited to, methanol, ethanol, water, tetrahydrofuran, 1,2-dimethoxyethane, and ethyl acetate. Preferably the reaction is carried out in ethanol using triethylamine as the base. The reaction temperature is generally 25° C. and reaction time is 1 to 12 hours.

Ketone of formula (6-1) can be further utilized by conversion into amine of formula (7-6) via a reductive amination. Reductive amination is achieved by treating the ketone with an amine in the presence of a reducing agent to obtain the product amine (7-6). The reaction can be carried out either with or without added acid. Examples of acids that are commonly used include, but are not limited to, hydrochloric, phosphoric, sulfuric, acetic, and the like. Reducing agents that effect reductive amination include, but are not limited to, hydrogen and a catalyst, zinc and hydrochloric acid, sodium cyanoborohydride, sodium borohydride, iron pentacarbonyl, and alcoholic potassium hydroxide. Generally alcoholic solvents are used. The preferred conditions use sodium cyanoborohydride in methanol with added acetic acid.

Yet another means by which to functionalize ketones of formula (6-1) is via addition of Grignard reagents to form alcohols of formula (7-5). The requisite Grignard reagents are readily available via the reaction of a variety of alkyl or aryl halides with magnesium under standard conditions (see B. S. Furniss, A. J. Hannaford, P. W. G. Smith, A. R. Tatchell, Vogel's Textbook of Practical Organic Chemistry, 5$^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In a similar way, reaction with other organometallic reagents gives rise to alcohols of formula (7-5). Examples of useful organometallic reagents include, but are not limited to, organo-aluminum, organo-lithium, organo-cerium, organo-zinc, organo-thallium, and organo-boron reagents. A more thorough discussion of organometallic reagents can be found in B. S. Furniss, A. J. Hannaford, P. W. G Smith, A. R. Tatchell, Vogel's Textbook of Practical Organic Chemistry. 5$^{th}$ ed., Longman, 1989.

Furthermore, alcohols of type (7-3) can be prepared by reduction of the corresponding ketone of formula (6-1) under a variety of conditions (see Hudlicky, M. Reductions in Organic Chemistry, Ellis Horwood Limited: Chichester, 1984). The alcohols thus derived can be further modified to give compounds of formula (7-4). A process to generate compounds of formula (7-4) includes, but is not limited to, J. Org. Chem., 1985, 2624–2626, (c) Maryanoff and Reitz, Chem. Rev, 1989, 863–927. Furthermore, vinyl halides of formula (7-7) can be functionalized by Sonogashira coupling with alkynes in the presence of a palladium catalyst, a copper halide and an amine base to give compounds of formula (7-8) (see (a) Sonogashira, Comprehensive Organic Synthesis, Volume 3, Chapters 2,4; (b) Sonogashira, Synthesis1977, 777.). In a similar manner, alkenes of formula (7-2) can be obtained from vinyl halides (7-7) via Suzuki-cross coupling with organoboron reagents in the presence of a palladium catalyst and a base, or via Stille cross coupling with organostananes in the presence of a palladium catalyst (see (a) Suzuki, J. Organomet. Chem. 1999, 576,147–168, (b) Stille, Angew Chem. Int. Ed. Engl., 1986, 508–524 (c) Farina, J. Am. Chem. Soc., 1991, 9585–9595).

It will be appreciated by one skilled in the art, that the unsaturated compounds represented by compounds (7-2) and (7-8) can be reduced to form the corresponding saturated compound (see Hudlicky, M., Reductions in Organic Chemistry, Ellis Horwood Limited: Chichester, 1984).

Scheme 8

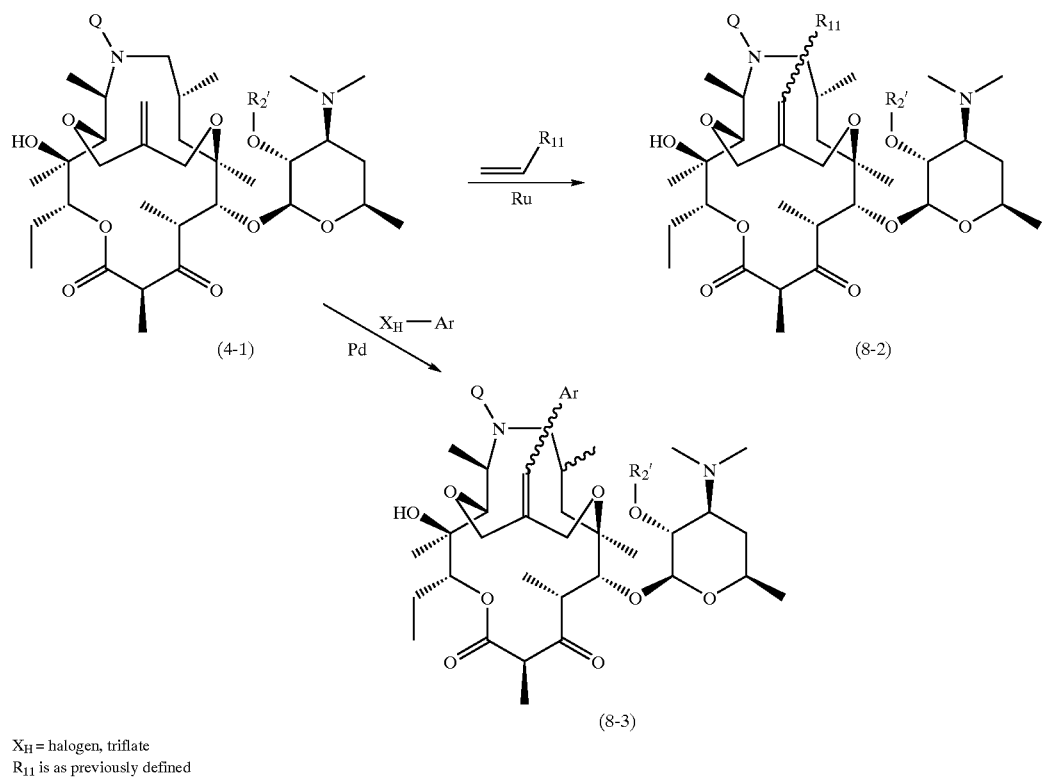

$X_H$ = halogen, triflate
$R_{11}$ is as previously defined alkylation of the alcohol with an electrophile or conversion of the alcohol into a leaving group, such as a triflate, tosylate, phosponate, halide, or the like, followed by displacement with a heteroatom nucleophile (e.g. an amine, alkoxide, sulfide or the like).

It will be appreciated by one skilled in the art that ketones of formula (6-1) can be transformed into alkenes of formula (7-2) and (7-7) via Wittig reaction with the appropriate phosphonium salt in the presence of a base, see (a) Burke, Tetrahedron Lett., 1987, 4143–4146, (b) Rathke and Nowak, Compounds of the invention according to formula (4-1) are also capable of further functionalization to generate compounds of the present invention. Alkene (4-1) can be treated with an aryl halide or aryl triflate in the presence of a palladium catalyst [Pd(O) or Pd(II)] to provide compound (8-3): (See (a) Heck, Palladium Reagents in Organic Synthesis, Academic Press: New York, 1985, Chapter 1; (b) Sonogashira, Comprehensive Organic Synthesis, Volume 3, Chapters 2,4; (c) Sonogashira, Synthesis 1977, 777). Under the Heck coupling conditions, regioisomers and stereoisomers of the double bond are possible. Alternatively, compound (4-1) can undergo a cross metathesis reaction with vinylaromatic derivatives using ruthenium catalysts to give compounds of formula (8-2) (see (a) *J. Org. Chem.* 2000, 65, 2204–2207; (b) Reviews: *Synlett*. 1999, 2, 267; (c) Reviews: Ivin, K. J.; Mol, J. C., *Olefin Metathesis and Metathesis Polymerization*, 2$^{nd}$ ed., Academic Press: New York, 1997; (d) *J. Org. Chem.* 1999, 64, 4798–4816; (e) *Angew. Chem., Int Ed. Engl.* 1997, 36, 2036–2056; (f) *Tetrahedron* 1998, 54, 4413–4450).

Scheme 9

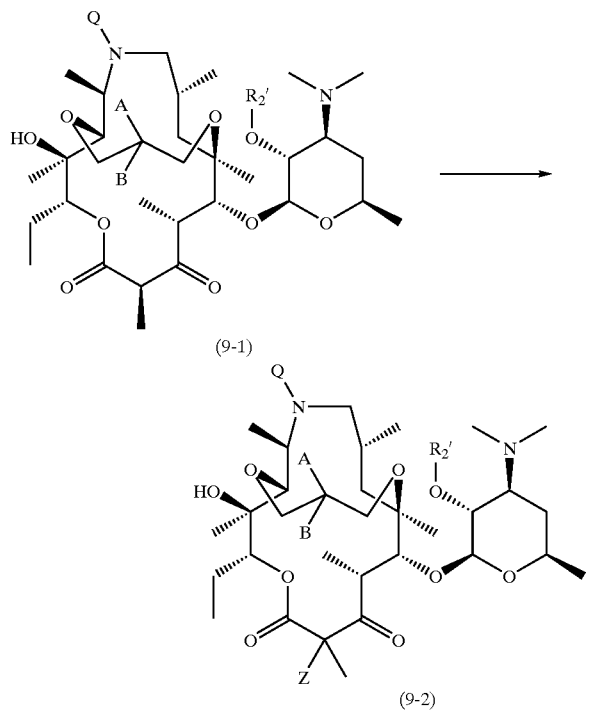

(9-1)

(9-2)

Scheme 7 illustrates the procedure by which compounds of formula (9-1), wherein A, B, Q, and $R_2'$ are as previously defined, may be converted to compounds of formula (9-2), wherein A, B, Q, Z, and $R_2'$ are as previously defined, by treatment with a halogenating reagent. This reagent acts to replace a hydrogen atom with a halogen atom at the C-2 position of the ketolide. Various halogenating reagents may be suitable for this procedure.

Fluorinating reagents include, but are not limited to, N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base.

Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence $Cl_2$, NaOCl in the presence of acetic acid.

Brominating reagents include, but are not limited to, $Br_2$.pyridine.HBr, $Br_2$/acetic acid, N-bromosuccinimide in the presence of base, $LDA/BrCH_2CH_2Br$, or $LDA/CBr_4$.

A suitable iodinating reagent is N-Iodosuccinimide in the presence of base, or $I_2$, for example.

Suitable bases for the halogenating reactions requiring them are compounds such as alkali metal hydrides, such as NaH and KH, or amine bases, such as LDA or triethylamine, for example. Different reagents may require different type of base, but this is well known within the art.

A preferred halogenating reagent is N-fluorobenzenesulfonimide in the presence of sodium hydride.

Suitable solvents are dimethylformamide, dimethyl sulfoxide, pyrrolidinone and the like.

It will be appreciated by one skilled in the art that all ketolide compounds delineated herein may be halogenated at the 2-carbon if so desired.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula I, Wherein A and B Taken Together With the Carbon Atom to Which They are Attached $=C=CH_2$, $D=-N(Q)CH_2-$, $Q=X=Z=H$, $Y=OH$, $L=CH_2CH_3$, $R_2'=Ac$ Step 1a: A compound of formula (1-2), wherein $R_7=R_2'=R_4''=Ac$.

To a solution of erythromycin A oxime (74.9 g, 0.1 mol) in 400 ml THF was added acetic anhydride (35.9 ml, 0.38 mol), triethylamine (55.7 ml, 0.4 mol) and DMAP (3.7 g, 0.03 mol) at room temperature. The mixture was stirred at room temperature for 16 hours, condensed to ~200 ml, diluted with 300 ml of ethyl acetate, the resulting mixture was washed with $NaHCO_3$ (Sat.) (500 ml×4) and brine (500 ml), and dried on anhydrous sodium sulfate. The solvent was evaporated in vacuo and the residue was recrystallized from ethyl acetate to give title compound (78 g).

MS (ESI) m/z 875.46 (M+H)$^+$. $^{13}$C NMR(CDCl$_3$): δ 178.5, 175.4, 170.6, 170.2, 168.2, 100.2, 96.1, 83.3, 79.3, 78.7, 75.2, 74.5, 72.9, 70.0, 67.6, 63.4, 63.2, 60.6, 49.5, 44.7, 40.9, 35.4, 31.8, 28.5, 22.8, 21.7, 21.6, 21.5, 21.3, 21.2, 21.1, 19.9, 18.6, 18.4, 16.7, 14.9, 14.4, 14.3, 10.8, 9.2.

Step 1b: A compound of formula (1-3), wherein $R_{11}=H$ and $R_{12}=t$-Bu.

To a solution of 2-methylene-1,3-propane diol (5.28 g, 0.06 mmol) and di-tert-butyl dicarbonate (35 g, 0.16 mol) in 150 ml of dichloromethane was added 6N NaOH (70 ml) and TBAHS (3.4 g, 10 mmol). The mixture was stirred at room temperature overnight. The organic layer was separated, washed with $NaHCO_3$ (200 ml×3) and brine (200 ml), dried over anhydrous $MgSO_4$, and concentrated in vacuo to give the title compound. $^1$H NMR (CDCl$_3$): δ 5.20(s, 2H); 4.44(s, 4H); 1.18(s, 18H). $^{13}$c NMR(CDCl$_3$): δ 153.28, 138.50, 117.27, 82.27, 66.91, 27.83.

Step 1c: A compound of formula (1-4), wherein $R_8$=Ac, $R_{11}$=H, $R_2'$=$R_4''$=Ac.

To a solution of erythromycin oxime 2', 4", 9-triacetate from Step 1a (112 g, 128 mmol), the compound from step 1b (44.3 g, 154 mmol) and dppb (1.71 g, 4 mmol) in THF (500 ml), was added $Pd_2(dba)_3$ (1.83 g, 2 mmol) under nitrogen. The mixture was refluxed for 5 hours and subsequently concentrated in vacuo. The residue was purified by flash chromatography ($SiO_2$ hexane:acetone/2:1) to give the title compound (110 g).

MS (ESI) m/z 927.64 $(M+H)^+$. $^{13}C$ NMR($CDCl_3$): δ 176.5, 175.9, 170.7, 170.1, 169.9, 141.6, 124.7, 100.4, 96.0, 79.1, 78.7, 78.2, 78.0, 77.4, 76.5, 73.5, 73.0, 72.4, 72.1, 67.8, 66.1, 63.4, 63.3, 49.6, 44.1, 41.2, 40.9, 37.3, 35.4, 35.1, 31.3, 29.5, 28.5, 27.1, 23.4, 21.7, 21.3, 21.1, 20.9, 20.3, 18.8, 18.3, 17.4, 15.7, 13.4, 12.7, 8.6.

Step 1d: A compound of formula (2-1), wherein $R_2'$=Ac.

To a solution of the compound from step 1c (23.2 g, 25 mmol) in 200 ml ethanol was added 2M HCl (40 ml). The mixture was heated to 78° C. and stirred for 1.5 hours. The mixture was condensed to 200 ml to which was added saturated $NaHCO_3$ (300 ml). The resulting mixture was then extracted with ethyl acetate (400 ml), washed with brine (300 ml×2), dried over anhydrous $Na_2SO_4$, and concentrated in vacuo. The residue was crystallized from acetonitrile to give the title compound (16.5 g, yield: 96%).

MS (ESI) m/z 685.84 $(M+H)^+$. $^{13}C$ NMR($CDCl_3$): δ 175.3, 170.2, 166.7, 143.9, 119.0, 99.7, 82.3, 79.6, 78.3, 78.2, 76.0, 74.2, 71.8, 69.1, 65.7, 63.5, 43.9, 40.9, 37.5, 36.0, 34.3, 31.2, 31.1, 25.6, 23.3, 21.7, 21.4, 20.0, 19.6, 17.1, 15.8, 14.8, 11.9, 7.9.

Step 1e: A compound of formula (3-1), wherein $R_2'$=Ac.

p-Toluenesulfonic anhydride (2.3 g, 7.0 mmol, 1.2 eq) was added to a solution of the compound of Step 1d (4 g, 5.8mrmol) and anhydrous $Et_3N$ (1.65 mL, 11.6 mmol, 2 eq) in $CH_2Cl_2$ (30 mL) at −10° C. The resulting mixture was stirred at −10° C. for 40 min. Anhydrous MeOH (4 mL) was added to the reaction mixture at −10° C., the reaction mixture was then slowly warmed to 20° C. and stirred for 1 hour. The reaction mixture was diluted with $CH_2Cl_2$ (100 mL), washed with saturated $NaHCO_3$ (3×100 mL), brine (100 mL), dried over $Na_2SO_4$, and concentrated in vacuo. The residue was purified by flash chromatography (Acetone/Hexanes=1/1) to give the title compound 2.9 g (75% yield).

MS (ESI) m/z 699.08 $(M+H)^+$.

Step 1f: A compound of formula (3-2), wherein $R_2'$=Ac.

A solution of compound from step 1e (105 mg, 0.15mmol) in 5 ml methanol was added $NaBH_4$ (17 mg, 0.5 mmol) at room temperature. The mixture was stirred at room temperature for 2 hours after which Tris (5%) (20 ml) was added and the resulting reaction mixture was stirred vigorously for 1 hour. The resulting mixture was extracted with ethyl acetate (30 ml) subsequently the organic phase was dried over $Na_2SO_4$ and concentrated in vacuo. The residue was purified on silica gel to give the title compound (80 mg).

MS (ESI) m/z 671.21 $(M+H)^+$.

Step 1g: A compound of formula (3-2), wherein $R_2'$=H.

A solution of the compound of Step 1f (80 mg) in 10 ml methanol was refluxed for 3 hours. The solvent was removed and the residue was purified by flash chromatography ($SiO_2$, 2M ammonia in methanol: $CH_2Cl_2$=5:95) to give the title compound (70 mg).

MS (ESI) m/z 629,12 $(M+H)^+$. $^{13}C$ NMR($CDCl_3$): δ 176.2, 143.2, 123.4, 106.4, 90.7, 81.5, 79.9, 79.8, 77.5, 74.9, 73.0, 70.6, 70.3, 66.7, 65.8, 61.0, 58.0, 53.7, 44.7, 44.1, 40.4, 36.3, 29.6, 28.1, 23.0, 22.4, 21.4, 20.7, 17.6, 17.4, 15.5, 11.7, 8.2.

Example 2

A Compound of Formula I, Wherein A and B Taken Together With the Carbon Atom to Which They are Attached =C=$CH_2$, D=—N(Q)$CH_2$—, Q=Z H, X and Y Taken Together =O, L=$CH_2CH_3$, $R_2'$=H To a solution of the title compound of Example 1 (25 mg) in 5 ml dichloromethane was added acetic acid (20 μl) and Dess-Martin periodiriane (15 mg) at room temperature. The mixture was stirred at room temperature for 30 minutes after which $Na_2S_{2O3}$ (20 mg) was added. The resulting reaction mixture was stirred for 1 hour, then to the mixture was added saturated $NaHCO_3$ (10 ml) and extracted with dichloromethane (10 ml). The extract was dried over anhydrous $Na_2SO_4$. The solvent was removed in vacuo and the residue was purified by flash chromatography ($SiO_2$, 2M ammonia in methanol: $CH_2Cl_2$=5:95) to give the title compound (20 mg).

MS (ESI) m/z 627.31 $(M+H)^+$. $^{13}C$ NMR($CDCl_3$): δ 206.5, 168.9, 142.1, 124.0, 103.1, 79.7, 79.0, 78.2, 77.5, 75.4, 74.6, 70.5, 70.4, 69.7, 66.4, 66.0, 60.0, 56.9, 50.5, 47.8, 43.4, 40.5, 29.6, 28.5, 23.2, 22.8, 21.5, 20.9, 17.8, 17.2, 15.2, 13.9, 12.4.

Example 3

A Compound of Formula I, Wherein A and B Taken Together With the Carbon Atom to Which They are Attached =C=$CH_2$, D=—N(Q)$CH_2$—, Q=$CH_3$, X=Z=H, Y=OH, L=$CH_2CH_3$, $R_2'$=H To a solution of the compound of Example 1 (63 mg, 0.1 mmol) in 10 ml methanol was added formaldehyde (37% in water) (100 μl), acetic acid (100 μl) and $NaCNBH_3$ (50 mg) at room temperature. The mixture was stirred at room temperature for 4 hours after which was added 5% Tris (30 ml). After stirring vigorously for 1 hour, the mixture was extracted with ethyl acetate (40 ml) and dried over anhydrous $Na_2SO_4$. The solvent was removed in vacuo and the residue was purified by flash chromatography ($SiO_2$, 2M ammonia in methanol:$CH_2Cl_2$=5:95) to give the title compound (60 mg).

MS (ESI) m/z 643.18$(M+H)^+$.

Example 4

A Compound of Formula I, Wherein A and B Taken Together With the Carbon Atom to Which They are Attached =C=$CH_2$, D=—N(Q)$CH_2$—, Q=$CH_3$, Z=H, X and Y Taken Together are oxo, L=$CH_2CH_3$, $R_2'$=H To a solution of the title compound of Example 2 (35 mg) in 5 ml dichloromethane was added acetic acid (20 ul) and Dess-Martin periodinane (20 mg) at room temperature. The resulting reaction mixture was stirred at room temperature for 4 hours after which was added $Na_2S_2O_3$ (20 mg). After stirring for 1 hour, to the mixture was added saturated $NaHCO_3$ (10 ml) and extracted with dichloromethane (10 ml). The extract was dried over anhydrous $Na_2SO_4$, the solvent was removed in vacuo and the residue was purified by flash chromatography ($SiO_2$, 2M ammonia in methanol: $CH_2Cl_2$=5:95) to give the title compound (25 mg).

MS (ESI) m/z 641.18 $(M+H)^+$. $^{13}C$ NMR($CDCl_3$): δ 206.7, 168.6, 143.3, 121.8, 103.6, 79.8, 78.9, 77.5, 77.3, 76.5, 70.6, 69.6, 68.4, 66.0, 65.3, 62.3, 53.7, 51.4, 47.5, 40.5, 29.6, 28.6, 24.6, 23.9, 21.5, 21.4, 17.6, 15.4,.14.8, 12.9.

Example 5

A Compound of Formula I, Wherein A=H, B=CH$_3$, D=—N(Q)CH$_2$—, Q=X=Z=H, Y=OH, L=CH$_2$CH$_3$, R2'=Ac A solution of compound from Step 1e (470 mg, 0.67 mmol) in acetic acid (5 ml) was kept under H$_2$ in the presence of PtO$_2$ (20 mg) for 2 days. The reaction mixture was filtered through celite, the filtrate was diluted with dichloromethane (50 ml); washed with saturated NaHCO$_3$ (2×50 ml) and brine (50 ml), and dried over anhydrous Na$_2$SO$_4$. The solvent was removed in vacuo and the residue was purified by flash chromatography (SiO$_2$, 2M ammonia in methanol:CH$_2$Cl$_2$=5:95) to give the title compound (120 mg).

MS (ESI) m/z 687.22 (M+H)$_+$.

Example 6

A Compound of Formula I, Wherein A=H, B=CH$_3$, D=—N(Q)CH$_2$—, Q=X=Z H, Y=OH, L=CH$_2$CH$_3$, R$_2$'=H A solution of compound of Example 5 (100 mg) in 10 ml methanol was refluxed for 3 hours. The solvent was removed in vacuo and the residue was purified by flash chromatography (SiO$_2$, 2M ammonia in methanol: CH$_2$Cl$_2$=5:95) to give the title compound (90 mg).

MS (ESI) m/z 631,17 (M+H)$^+$.

$^{13}$C NMR(CDCl$_3$): δ 176.2, 106.3, 90.1, 80.84, 80.78, 79.8, 77.6, 74.2, 70.6, 70.3, 68.5, 65.8, 64.0, 60.3, 44.8, 43.5, 40.4, 37.1, 36.1, 31.8, 28.7, 28. 1, 22.8, 22.6, 21.7, 21.4, 20.1, 16.7, 16.1, 15.5, 14.3, 11.4, 8.1.

Example 7

A Compound of Formula I, Wherein A=H, B=CH$_3$, D=—N(Q)CH$_2$, Q=Z=H. X and Y Taken Together are oxo, L=CH$_2$CH$_3$, R$_2$'=H A solution of the title compound of Example 6 (12 mg) in 2 ml dichloromethane was added acetic acid (20 μl) and Dess-Martin periodinane (32 mg) at room temperature. The mixture was stirred at room temperature for 2 hours after which was added Na$_2$S$_2$O$_3$ (20 mg). After stirring for 1 hour, saturated NaHCO$_3$ (10 ml) was added, the resulting mixture was then extracted with dichloromethane (5 ml) and dried over anhydrous Na$_2$SO$_4$. The solvent was removed in vacuo and the residue was purified by flash chromatography (SiO$_2$, 2M ammonia in methanol: CH$_2$Cl$_2$=5:95) to give the title compound (7 mg).

MS (ESI) m./z 629.27 (M+H)$^+$.

Example 8

A Compound of Formula I, Wherein A=H, B=CH$_3$, D=—N(Q)CH$_2$—, Q=CH$_3$, X=Z=H, Y=OH, L=CH$_2$CH$_3$, R$_2$'=H To a solution of the title compound from Example 6 (10 mg) in 2 ml methanol was added formaldehyde (37% in water) (20 μl), acetic acid (30 μl) and NaCNBH$_3$ (10 mg) at room temperature. The mixture was stirred at room temperature for 4 hours after which was added 5% Tris (10 ml). After vigorously stirred for 1 hour, the mixture was extracted with ethyl acetate (10 ml) and dried over anhydrous Na$_2$SO$_4$.

The solvent was removed and the residue was purified by flash chromatography (SiO$_2$, 2M ammonia in methanol: CH$_2$Cl$_2$=5:95) to give the title compound (10 mg).

MS (ESI) m/z 645.28(M+H)$^+$.

Example 9

A Compound of Formula I, Wherein A=H, B=CH$_3$, D=—N(Q)CH$_2$—, Q=CH$_3$, Z=H, X and Y Taken Together are oxo. L=CH$_2$CH$_3$, R$_2$'=H To a solution of the compound of Example 8 (10 mg) in 2 ml dichloromethane was added acetic acid (20 μl) and Dess-Martin periodinane (20 mg) at room temperature. The mixture was stirred at room temperature for 2 hours after which was added Na$_2$S$_{2O3}$ (25 mg). After stirring for 1 hour, to the mixture was added saturated NaHCO$_3$ (10 ml). The mixture was then extracted with dichloromethane (5 ml), dried over anhydrous Na$_2$SO$_4$, and concentrated in vacuo. The resulting residue was purified by flash chromatography (SiO$_2$, 2M ammonia in methanol: CH$_2$Cl$_2$=5:95) to give the title compound (6 mg).

MS (ESI) m/z 643.35(M+H)$^+$.

Example 10

A Compound of Formula I, Wherein A=H, B=CH$_3$, D=—(C=NOH)—, Z=X=H,

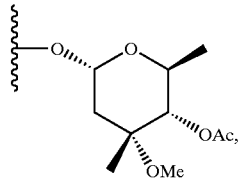

L=CH$_2$CH$_3$, R$_2$'=Ac

To a solution of the compound from step 1c (456 mg, 0.46 mmol) in a 1:1 mixture of THF-iPrOH (5 ml) at 0° C. was added 1 N LiOH (2.5 ml). The reaction mixture was stirred at 0° C. for 30 minutes after which was added saturated NaHCO$_3$ (10 ml). The resulting mixture was extracted with ethyl acetate (10 ml×2), the organic layers were dried over Na$_2$SO$_4$, the solvent was removed in vacuo, and the residue was purified via flash chromatography (SiO$_2$, hexane/acetone=2/1) to give the title compound (433 mg).

MS (ESI) m/z 885.29(M+H)$^+$.

$^{13}$C NMR(CDCl$_3$): δ 175.9, 170.6, 170.1, 168.3, 141.9, 124.1, 100.5, 95.9, 79.3, 78.9, 78.0, 75.2, 74.5, 72.9, 72.7, 71.9, 71.6, 67.6, 65.5, 63.4, 63.2, 60.5, 49.5, 44.0, 41.3, 40.8, 37.3, 34.9, 34.3, 31.2, 31.0, 29.4, 25.7, 23.4, 21.6, 21.2, 21.0, 18.9, 18.1, 17.5, 15.3, 13.1, 12.7, 8.5.

Example 11

A Compound of Formula I, Wherein A=H, B=CH$_3$, D=—NH(C=O)—, Z=X=H,

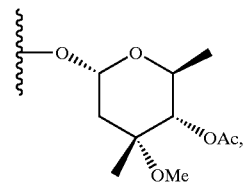

L=CH2CH$_3$, R$_2'$=Ac

To a solution of the compound from step 1a (120 mg, 0.13 mmol) in acetone was added a solution of TsCl (49 mg, 0.27 mmol) in 0.4 ml acetone and a solution of NaHCO$_3$ (44 mg, 0.52 mmol) in 1.4 ml water at 0° C. The reaction mixture was stirred at 0° C. for 2 hours and cooled to room temperature for overnight. The reaction mixture was then diluted with 15 ml methylene chloride, washed with brine (20 ml×2), and dried over sodium sulfate. The solvent was subsequently removed in vacuo and the residue was purified by flash chromatography (SiO$_2$, hexane/acetone=1/1) to give the title compound (70 mg).

MS (ESI) m/z 885.44(M+H)$^+$. $^{13}$C NMR(CDCl$_3$): δ 178.9, 176.8, 170.8, 170.2, 135.7, 131.9, 100.6, 94.5, 79.9, 79.1, 78.7, 78.5, 76.3, 75.1, 74.3, 73.0, 72.0, 70.8, 67.6, 63.4, 62.9, 61.5, 49.6, 45.7, 45.5, 42.5, 40.9, 39.5, 37.2, 35.1, 31.7, 31.1, 29.4, 22.0, 21.7, 21.6, 21.5, 21.4, 21.1, 20.9, 18.3, 15.1, 14.5, 11.3, 9.3.

Example 12

A Compound of Formula I, Wherein A=H, B=CH$_3$, —NH(C=O)—, Z=X=H,

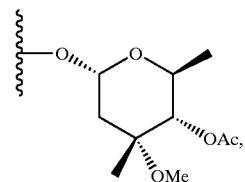

L=CH$_2$CH$_3$, R$_2'$=H

A solution of compound of example 1b (70 mg) in 10 ml methanol was refluxed for 3 hours. The solvent was removed and the residue was purified by flash chromatography (SiO$_2$, 2M ammonia in methanol: CH$_2$Cl$_2$=5:95) to give the title compound (60 mg).

Example 13

A Compound of Formula I, Wherein A and B Taken Together With the Carbon Atom to Which They are Attached is C=CH$_2$, D=—N(Q)CH$_2$—, Q=CH$_2$Ph, Z=X=H, Y=OH, L=CH$_2$CH$_3$ R$_2'$=H A solution of the compound of Example 2 in MeOH is treated with benzaldehyde, excess NaCNBH$_3$, and acetic acid at room temperature. The reaction mixture is stirred at room temperature for 4–8 hours and subsequently cooled to 0° C. The solution is then neutralized with aqueous NaHCO$_3$, extracted with methylene chloride, and the organic phase is dried over Na$_2$SO$_4$. The solvents are removed in vacuo and the residue is purified via column chromatography on silica gel to provide the title compound.

Example 14

A Compound of Formula I, Wherein A and B Taken Together With the Carbon Atom to Which They are Attached =C=CH, D=—N(Q)CH$^2$—, Q=CH$_2$Ph, Z=H, X and Y are Taken Together are oxo, L=CH$_2$CH$_3$, R$_2'$=H The title compound is prepared with the title compound of Example 13 via the Dess-Martin oxidation conditions described in Example 9.

Example 15

A Compound of Formula I, Wherein A and B Taken Together With the Carbon Atom to Which They are Attached =C=CH$_2$, D=—N(Q)CH$_2$—, Q=CH$_2$(2-Pyridyl), Z=X=H, Y=OH, L=CH$_2$CH$_3$, R$_2'$=H The title compound is prepared via the procedure set forth in Example 13 with the title compound of Example 2 and 2-pyridine carboxaldehyde.

Example 16

A Compound of Formula I, Wherein A and B Taken Together With the Carbon Atom to Which They are Attached =C=CH$_2$, D=—N(Q)CH$_2$—, Q=CH$_2$(2-Pyridyl), Z=H, X and Y Taken Together are oxo, L=CH$_2$CH$_3$, R$_2'$=H The title compound is prepared with the title compound of Example 15 via the Dess-Martin oxidation conditions described in Example 9.

Example 17

A Compound of Formula I, Wherein A and B Taken Together With the Carbon Atom to Which They are Attached =C=CH$_2$, D=—N(Q)CH$_2$—, Q=CH$_2$(3-quinolyl), Z=H, X and Y Taken Together are oxo, L=CH$_2$CH$_3$, R$_2$=H The title compound is prepared via the procedure set forth in Example 13 with the title, compound of Example 2 and 3-quinoline carboxaldehyde.

Example 18

A Compound of Formula I, Wherein A and B Taken Together With the Carbon Atom to Which They are Attached =C=CH$_2$, D=—N(Q)CH$_2$—, Q=CH$_2$(3-guinolyl), Z=H, X and Y taken together are oxo, L=CH$_2$CH$_3$, R$_2'$=H The title compound is prepared with the title compound of Example 13 via the Dess-Martin oxidation conditions described in Example 9.

Example 19

A Compound of Formula I, Wherein A and B Taken Together With the Carbon Atom to Which They are Attached =C=CH$_2$, D=—N(Q)CH$_2$—, Q=CH$_2$(CH=CH)Ph, Z=X=H, Y=OH, L=CH$_2$CH$_3$, R$_2'$=H The title compound is prepared via the procedure set forth in Example 13 with the title compound of Example 2 and cinnamaldehyde.

Example 20

A Compound of Formula I, Wherein A and B Taken Together With the Carbon Atom to Which They are Attached =C=CH$_2$, D=—N(Q)CH$_2$—, Q=CH$_2$(CH=CH)Ph, Z=H, X and Y Taken Together are oxo, L=CH$_2$CH$_3$, R$_2$'=H The title compound is prepared with the title compound of Example 19 via the Dess-Martin oxidation conditions described in Example 9.

Example 21

A Compound of Formula I, Wherein A and B Taken Together With the Carbon Atom to Which They are Attached =C=CH$_2$, D=—N(Q)CH$_2$—, Q=CH$_2$CH=CH(2-pyridyl), Z=X=H, Y=OH, L=CH$_2$CH$_3$, R$_2$'=H The title compound is prepared via the procedure set forth in Example 13 with the title compound of Example 2 and 3-(2-pyridyl)acrolein.

Example 22

A Compound of Formula I, Wherein A and B Taken Together With the Carbon Atom to Which They are Attached =C=CH$_2$, D=—N(Q)CH$_2$—, Q=CH$_2$CH=CH(2-pyridyl), Z=H, X and Y Taken Together are oxo, L=CH$_2$CH$_3$, R$_2$'=H The title compound is prepared with the title compound of Example 21 via the Dess-Martin oxidation conditions described in Example 9.

Example 23

A Compound of Formula I, Wherein A and B Taken Together With the Carbon Atom to Which They are Attached =C=CH$_2$, D=—N(Q)CH$_2$—, Q=CH$_2$C≡C(3-guinolyl), Z=H, X and Y taken together are oxo, L=CH$_2$CH$_3$, R$_2$'=H The title compound is prepared via the procedure set forth in Example 13 with the title compound of Example 2 and 3-(3-quinolyl)propynaldehyde.

Example 24

A Compound of Formula I, Wherein A and B Taken Together With the Carbon Atom to Which They are Attached =C=CH$_2$, D=—N(Q)CH$_2$—, Q=CH$_2$C≡C(3-guinolyl), Z=H, X and Y Taken Together are oxo, L=CH$_2$CH$_3$, R$_2$'=H The title compound is prepared with the title compound of Example 23 via the Dess-Martin oxidation conditions described in Example 9.

Example 25

A Compound of Formula I, Wherein A and B Taken Together With the Carbon Atom to Which They are Attached =C=CH—CH=CHPh, D=—N(Q)CH$_2$—, Q=CH$_3$, Z=H, X and Y Taken Together are oxo, L=CH$_2$CH$_3$, R$_2$'=H To a solution of the compound of Example 4 (0.5 g, 0.7 mmol) in 8 ml anhydrous DMF, β-bromostyrene (0.15 ml, 1.2 mmol) and K$_2$CO$_3$ (200 mg, 1.5 mmol) are added at room temperature. The mixture is degassed briefly and a catalytic amount of POPd is added. The reaction mixture is heated to 100° C. in a sealed tube for 48 hours. Ethyl acetate (50 mL) is added and the solution is washed 3 times with aqueous NaHCO$_3$. The organic layer is dried over anhydrous Na$_2$SO$_4$. The solvent is evaporated under vacuum and the residue is purified by flash chromatography (SiO$_2$, acetone:hexanes/1:1) to provide the title compound.

Example 26

A Compound of Formula I, Wherein A and B Taken Together With the Carbon Atom to Which They are Attached =C=CH—CH=CH(3-pyridyl), D=—N(Q)CH$_2$—, Q=CH$_3$, Z=H, X and Y Taken Together are oxo, L=CH$_2$CH$_3$, R$_2$'=H The title compound is prepared with the title compound of Example 4 with 1-bromo-2-(3-pyridyl)ethylene via the Heck conditions set forth in Example 25.

Example 27

A Compound of Formula I, Wherein A and B Taken Together With the Carbon Atom to Which They are Attached =C=CH—CH=CH(3-guinolyl), D=—N(Q)CH$_2$—, Q=CH$_3$, Z=H, X and Y Taken Together are oxo, L=CH$_2$CH$_3$, R$_2$'=H The title compound is prepared with the title compound of Example 4 with 1-bromo-2-(3-quinolyl)ethylene via the Heck conditions set forth in Example 25.

Example 28

A Compound of Formula I, Wherein A and B Taken Together With the Carbon Atom to Which They are Attached =C=CH-3-guinolyl, D=—N(Q)CH$_2$—, Q=CH$_3$, Z=H, X and Y Taken Together are oxo, L=CH2CH$_3$, R$_2$'=H The title compound is prepared with the title compound of Example 4 with 3-bromoquinoline via the Heck conditions set forth in Example 25.

Example 29

A Compound of Formula I, Wherein A and B Taken Together With the Carbon Atom to Which They are Attached =C=CH—Ph, D=—N(Q)CH$_2$—, Q=CH$_3$, Z=H, X and Y Taken Together are oxo, L=CH$_2$CH$_3$, R$_2$'=H The title compound is prepared with the title compound of Example 4 with bromobenzene via the Heck conditions set forth in Example 25.

Example 30

A Compound of Formula I, Wherein A and B Taken Together With the Carbon Atom to Which They are Attached are C=O, D=—N(Q)CH$_2$—, Q=CH$_3$, X and Y Taken Together are oxo, L=CH$_2$CH$_3$, Z=H, and R$_2$'=H A solution of the compound of Example 4 (0.15 mmol) in 2 ml of methanol and 4 ml of CH$_2$Cl$_2$ is purged with O$_3$ at −78° C. until the solution becomes light blue. Nitrogen is bubbled through the solution to remove excess O$_3$ and then PPh₃ (2 eq) is added. The resulting reaction mixture is warmed to room temperature and stirred at room temperature for 2 hours. The mixture is then concentrated in vacuo, the residue is dissolved in 5 ml of THF, and an additional 2 eq of PPh₃ is added. The resulting mixture is refluxed overnight and concentrated in vacuo. The residue is purified by flash chromatography (SiO₂, CH₂Cl₂:2M ammonia in methanol/95:5) to give the title compound.

Example 31

Compound of Formula I: A and B Taken Together With the Carbon Atom to Which They are Attached are C=N—O—CH₂Ph, X and Y Taken Together are oxo, L=CH₂CH₃, Z=H, and R₂'=H A solution of the crude compound from Example 30 (0.05 mmol), benzyl. hydroxylamine (0.1 mmol) and pyridinre (0.2 mmol) in 4 ml ethanol is stirred at room temperature for 1 hour. The reaction mixture is then concentrated in vacuo and purified by flash chromatography (SiO₂, CH₂C₁₂:2M ammonia in methanol=95:5) to give the title compound (3:1 cis and trans mixture).

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:
1. A compound of formula I, or a pharmaceutically acceptable salt, ester, or prodrug thereof:

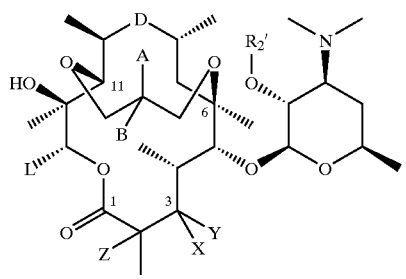

(I)

wherein,
A is
  i) —OH;
  ii) —OR$_p$, where R$_p$ is a hydroxy protecting group;
  iii) —R₁, where R₁ is aryl, substituted aryl, heteroaryl, or substituted heteroaryl;
  iv) —OR₁, where R₁ is as previously defined;
  v) —R₂, where R₂ is
    (a) hydrogen;
    (b) halogen;
    (c) —C₁–C₆ alkyl containing 0, 1, 2, or 3 heteroatoms selected from O, S or N, optionally substituted with one or more substituents selected from halogen, aryl, substituted aryl, heteroaryl, or substituted heteroaryl;
    (d) —C₂–C₆ alkenyl containing 0, 1, 2, or 3 heteroatoms selected from O, S, or N, optionally substituted with one or more substituents selected from halogen, aryl, substituted aryl, hetbroaryl, or substituted heteroaryl; or
    (e) —C₂–C₆ alkynyl containing 0, 1, 2, or 3 heteroatoms selected from O, S or N, optionally substi-
tuted with one or more substituents selected from halogen, aryl, substituted aryl, heteroaryl, or substituted heteroaryl;
  vi) —OR₂, where R₂ is previously defined;
  vii) —S(O)$_n$R₁₁, where n=0, 1 or 2, and R₁₁ is R₁ or R₂, where R₁ and R₂ are previously defined;
  viii) —NHC(O)R₁₁, where R₁₁ is as previously defined;
  ix) —NHC(O)NHR₁₁, where R₁₁ is as previously defined;
  x) —NHS(O)₂R₁₁, where R₁₁ is as previously defined;
  xi) —NR₁₄R₁₅, where R₁₄ and R₁₅ are each independently R₁₁, where R₁₁ is as previously defined; or
  xii) —NHR₃, where R₃ is an amino protecting group;
B is
  i) hydrogen;
  ii) deuterium;
  iii) halogen;
  iv) —OH;
  v) —R₁, where R₁ is as previously defined;
  vi) —R₂, where R₂ is as previously defined; or
  vii) —OR$_p$, where R$_p$ is as previously defined, provided that when B is halogen, —OH or OR$_p$, A is R₁ or R₂;
or, alternatively, A and B taken together with the carbon atom to which they are attached are
  i) C=O;
  ii) C(OR₂)₂, where R₂ is as previously defined;
  iii) C(SR₂)₂, where R₂ is as previously defined;
  iv) C[—O(CH₂)$_m$]₂, where m=2 or 3;
  v) C[—S(CH₂)$_m$]₂, where m is as previously defined;
  vi) C=CHR₁₁, where R₁₁ is as previously defined;
  vii) C=N—O—R₁₁, where R₁₁ is as previously defined;
  viii) C=NNHR₁₁, where R₁₁ is as previously defined;
  ix) C=NNHC(O)R₁₁, where R₁₁ is as previously defined;
  x) C=NNHC(O)NHR₁₁, where R₁₁ is as previously defined;
  xi) C=NNHS(O)₂R₁₁, where R₁₁ is as previously defined;
  xii) C=NNHR₃, where R₃ is as previously defined; or
  xiii) C=NR₁₁, where R₁₁ is as previously defined;
L is
  i) —CH₃;
  ii) —CH₂CH₃;
  iii) —CH(OH)CH₃;
  iv) —C₁-C₆ alkyl, optionally substituted with one or more substituents selected from aryl, substituted aryl, heteroaryl, or substituted heteroaryl;
  v) —C₂-C₆ alkenyl, optionally substituted with one or more substituents selected from aryl, substituted aryl, heteroaryl, or substituted heteroaryl; or
  vi) —C₂-C₆ alkynyl, optionally substituted with one or more substituents selected from aryl, substituted aryl, heteroaryl, or substituted heteroaryl;
D is —N(Q)CH₂—, —N(R')C(O)—, or —N=C(OR')—, wherein R' is R¹¹ as previously defined and Q is defined herein;
Q is
  i) hydrogen;
  ii) —C₁–C₁₂-alkyl, C₃–C₁₂-alkenyl, or C₃–C₁₂-alkynyl, all optionally substituted with one or more substituents independently selected from:
    (a) halogen;
    (b) —OR₆, wherein R₆ is selected from:
      1. hydrogen;

2. —$C_1$–$C_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
3. aryl;
4. substituted aryl;
5. heteroaryl; and
6. substituted heteroaryl;

(c) —$NR_4R_5$, where $R_4$ and $R_5$ are each independently $R_6$, where $R_6$ is as previously defined; or in the alternative $R_4$ and $R_5$, together with the atom to which they are attached, form a heterocycloalkyl or substituted heterocycloalkyl moiety;
(d) =N—O—$R_6$, where $R_6$ is as previously defined;
(e) —$R_1$, where $R_1$ is as previously defined;
(f) —$C_3$–$C_8$-cycloalkyl;
(g) substituted —$C_3$–$C_8$-cycloalkyl;
(h) heterocycloalkyl;
(i) substituted heterocycloalkyl;
(j) —NHC(O)$R_6$, where $R_6$ is as previously defined;
(k) —NHC(O)O$R_7$, where $R_7$ is selected from:
  1. —$C_1$–$C_{12}$-alkyl containing 0, 1, 2, or 3 heteroatoms selected from O, S or N, optionally substituted with one, two, or three substituents independently selected from aryl, substituted aryl, heteroaryl, or substituted heteroaryl;
  2. aryl;
  3. substituted aryl;
  4. heteroaryl; or
  5. substituted heteroaryl;
(l) —NHC(O)$NR_4R_5$, where $R_4$ and $R_5$ are as previously defined;
(m) —OC(O)$NR_4R_5$, where $R_4$ and $R_5$ are as previously defined;
(n) —OC(O)$R_7$, where $R_7$ is as previously defined;
(o) —OC(O)O$R_7$, where R7 is as previously defined;
(p) —OC(O)$NR_4R_5$, where $R_4$ and $R_5$ are as previously defined;
(q) —C(O)$R_6$, where $R_6$ is as previously defined;
(r) —$CO_2R_6$, where $R_6$ is as previously defined; or
(s) —C(O)$NR_4R_5$, where $R_4$ and $R_5$ are as previously defined;

X is hydrogen;
Y is
i) hydrogen;
ii) —OH;
iii) —$OR_p$, where $R_p$ is as previously defined;
iv) —$OR_{11}$, where $R_{11}$ is as previously defined;
v) —OC(O)$R_{11}$, where $R_{11}$ is as previously defined;
vi) —OC(O)NH$R_{11}$, where $R_{11}$ is as previously defined;
vii) —S(O)$_n R_{11}$, where n and $R_{11}$ are as previously defined;
viii) —

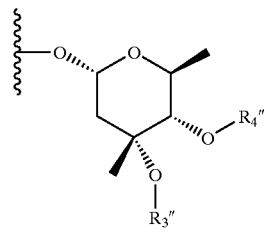

where $R_3''$ is hydrogen or methyl; $R_4''$ is hydrogen or $R_p$, where $R_p$ is as previously defined; or in the alternative X and Y combined together are oxo;
Z is
i) hydrogen;
ii) methyl; or
iii) halogen; and
$R_2'$ is hydrogen or $R_p$, where $R_p$ is as previously defined.

2. A compound of the formula I as defined in claim 1, wherein D is —N(Q)$CH_2$—.

3. A compound of the formula I as defined in claim 1, wherein D is —N(Q)$CH_2$—, X is hydrogen, and Y is

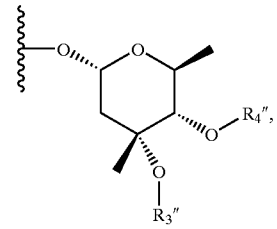

wherein $R_3''$ and $R_4''$ is as defined in claim 1.

4. A compound of the formula I as defined in claim 1, wherein D is —N(Q)$CH_2$— and X and Y taken together are oxo.

5. A compound of the formula I as defined in claim 1, wherein D is —N=CH(OR')—, wherein R' is as defined in claim 1.

6. A compound of the formula I as defined in claim 1, wherein D is —N(R')C(O)—, wherein R' is as defined in claim 1.

7. A compound according to claim 1 selected from:
i) A compound of formula I, wherein A and B taken together with the carbon atom to which they are attached is C=$CH_2$, D is —N(Q)$CH_2$—, Q=X=Z=H, Y=OH, L=$CH_2CH_3$, $R_2'$=Ac;
ii) A compound of formula I, wherein A and B taken together with the carbon atom to which they are attached is C=$CH_2$, D=—N(Q)$CH_2$—, Q=Z=H, X and Y taken together are oxo, L=$CH_2CH_3$, $R_2'$=H;
iii) A compound of formula I, wherein A and B taken together with the carbon atom to which they are attached are C=$CH_2$, D=—N(Q)$CH_2$—, Q=$CH_3$, X=Z=H, Y=OH, L=$CH_2CH_3$, $R_2'$=H;
iv) A compound of formula I, wherein A and B taken together with the carbon atom to which they are attached are C=$CH_2$, D=—N(Q)$CH_2$—, Q=$CH_3$, Z=H, X and Y taken together are oxo, L=$CH_2CH_3$, $R_2'$=H;
v) A compound of formula I, wherein A=H, B=$CH_3$, D=—N(Q)$CH_2$—, Q=X=Z=H, Y=OH, L=$CH_2CH_3$, $R_2'$=Ac;
vi) A compound of formula I, wherein A=H, B=$CH_3$, D=—N(Q)$CH_2$—, Q=X=Z=H, Y=OH, L=$CH_2CH_3$, $R_2'$=H;
vii) A compound of formula I, wherein A=H, B=$CH_3$, D=—N(Q)$CH_2$—, Q=Z=H, X and Y taken together are oxo, L=$CH_2CH_3$, $R_2'$=H;
viii) A compound of formula I, wherein A=H, B=$CH_3$, D=—N(Q)$CH_2$—, Q=$CH_3$, X=Z=H, Y=OH, L=$CH_2CH_3$, $R_2'$=H;
ix) A compound of formula I, wherein A=H, B=$CH_3$, D=—N(Q)$CH_2$—, Q=$CH_3$, Z=H, X and Y taken together are oxo, L=$CH_2CH_3$, $R_2'$=H;
x) A compound of formula I, wherein A=H, B=$CH_3$, D=—(C=NOH)—, X=Z=H, Y=

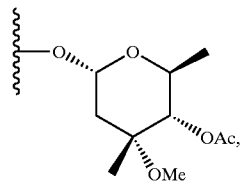

L=CH₂CH₃, R₂'=H;

xi) A compound of formula I, wherein A=H, B=CH₃, D=—NH(C=O)—, X=Z=H, Y=

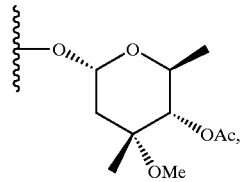

L=CH₂CH₃, R₂'=H;

xii) A compound of formula I, wherein A=H, B=CH₃, D=—NH(C=O)—, X=Z=H, Y=

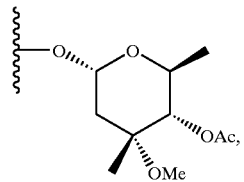

L=CH₂CH₃, R₂'=H;

xiii) A compound of formula I, wherein A and B taken together with the carbon atom to which they are attached =C=CH₂, D=—N(Q)CH₂—, Q=CH₂Ph, Z=X=H, Y=OH, L=CH₂CH₃, R₂'=H;

xiv) A compound of formula I, wherein A and B taken together with the carbon atom to which they are attached =C=CH₂, D=—N(Q)CH₂—, Q=CH₂Ph, Z=H, X and Y are taken together are oxo, L=CH₂CH₃, R₂'=H;

xv) A compound of formula I, wherein A and B taken together with the carbon atom to which they are attached =C=CH₂, D=—N(Q)CH₂—, Q=CH₂(2-pyridyl), Z=X=H, Y=OH, L=CH₂CH₃, R₂'=H;

xvi) A compound of formula I, wherein A and B taken together with the carbon atom to which they are attached =C=CH₂, D=—N(O)CH₂—, Q=CH₂(2-pyridyl), Z=H, X and Y taken together are oxo, L=CH₂CH₃, R₂'=H;

xvii) A compound of formula I, wherein A and B taken together with the carbon atom to which they are attached =C=CH₂, D=—N(Q)CH₂—, Q=CH₂(3-quinolyl), Z=H, X and Y taken together are oxo, L=CH₂CH₃, R₂'=H;

xviii) A compound of formula I, wherein A and B taken together with the carbon atom to which they are attached =C=CH₂, D=—N(Q)CH₂—, Q=CH₂(3-quinolyl), Z=H, X and Y taken together are oxo, L=CH₂CH₃, R₂'=H;

xix) A compound of formula I, wherein A and B taken together with the carbon atom to which they are attached =C=CH₂, D=—N(Q)CH₂—, Q=CH₂(CH=CH)Ph, Z=X=H, Y=OH, L=CH₂CH₃, R₂'=H;

xx) A compound of formula I, wherein A and B taken together with the carbon atom to which they are attached =C=CH₂, D=—N(O)CH₂—, O =CH₂(CH=CH)Ph, Z=H, X and Y taken together are oxo, L=CH₂CH₃, R₂'=H;

xxi) A compound of formula I, wherein A and B taken together with the carbon atom to which they are attached =C=CH₂, D=—N(Q)CH₂—, Q=CH₂CH=CH(2-pyridyl), Z=X=H, Y=OH, L=CH₂CH₃, R₂'=H;

xxii) A compound of formula I, wherein A and B taken together with the carbon atom to which they are attached =C=CH₂, D=—N(Q)CH₂—, Q=CH₂CH=CH(2-pyridyl), Z=H, X and Y taken together are oxo, L=CH₂CH₃, R₂'=H;

xxiii) A compound of formula I, wherein A and B taken together with the carbon atom to which they are attached =C=CH₂, D=—N(Q)CH₂—, Q=CH₂C=—C(3-quinolyl), Z=H, X and Y taken together are oxo, L=CH₂CH₃, R₂'=H;

xxiv) A compound of formula I, wherein A and B taken together with the carbon atom to which they are attached =C=CH₂, D=—N(Q)CH₂—, Q=CH₂C=C(3-quinolyl), Z=H, X and Y taken together are oxo, L=CH₂CH₃, R₂'=H;

xxv) A compound of formula I, wherein A and B taken together with the carbon atom to which they are attached =C=CH—CH=CHPh, D=—N(Q)CH₂—, Q=CH₃, Z=H, X and Y taken together are oxo, L=CH₂CH₃, R₂'=H;

xxvi) A compound of formula I, wherein A and B taken together with the carbon atom to which they are attached =C=CH—CH=CH(3-pyridyl), D=—N(Q)CH₂—, Q=CH₃, Z=H, X and Y taken together are oxo, L=CH₂CH₃, R₂'=H;

xxvii) A compound of formula I, wherein A and B taken together with the carbon atom to which they are attached =C=CH—CH=CH(3-quinolyl), D=—N(Q)CH₂—, Q=CH₃, Z=H, X and Y taken together are oxo, L=CH₂CH₃, R₂'=H;

xxviii) A compound of formula I, wherein A and B taken together with the carbon atom to which they are attached =C=CH₃-quinolyl, D=—N(Q)CH₂—, Q=CH₃, Z=H, X and Y taken together are oxo, L=CH₂CH₃, R₂'=H; or xxix) A compound of formula I, wherein A and B taken together with the carbon atom to which they are attached =C=CH—Ph, D=—N(Q)CH₂—, Q=CH₃, Z=H, X and Y taken together are oxo, L=CH₂CH₃, R₂'=H.

8. A pharmaceutical composition comprising a therapeutically effective amount of a compound of claim 1 or a pharmaceutically acceptable salt, ester or prodrug thereof, in combination with a pharmaceutically acceptable carrier.

9. A method for controlling a bacterial infection in a subject, comprising administering to said subject a therapeutically effective amount of a pharmaceutical composition according to claim 8.

10. A process for the preparation of a compound of formula:

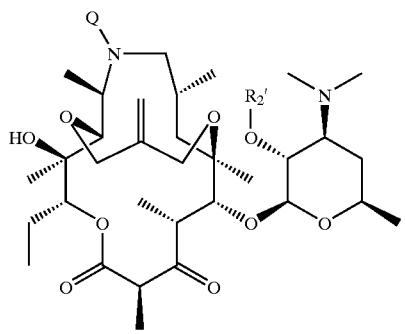

wherein Q and R$_2$' are as defined in claim 1, comprising the steps of:
(1) reacting a compound of the formula:

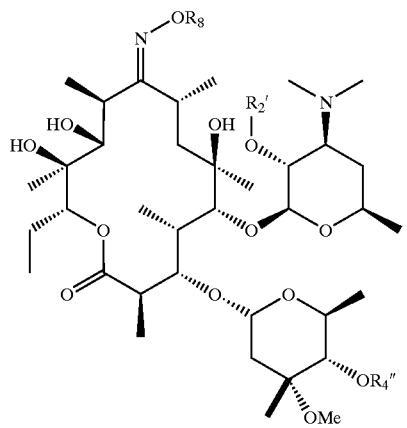

wherein
R$^8$ is
  a. Hydrogen;
  b. —CH$_2$O(CH$_2$)$_2$OCH$_3$;
  c. —CH$_2$O(CH$_2$O)$_n$CH$_3$, where n is as previously defined;
  d. —C$_1$–C$_{12}$ alkyl, optionally substituted with one or more substituents selected from aryl, substituted aryl, heteroaryl and substituted heteroaryl;
  e. —C$_3$–C$_{12}$ cycloalkyl;
  f. —C(O)—C$_1$–C$_{12}$ alkyl;
  g. —C(O)—C$_3$–C$_{12}$ cycloalkyl;
  h. —C(O)—R$_1$, where R$_1$ is as previously defined; or
  i. —Si(R$_a$)(R$_b$)(R$_c$), wherein R$_a$, R$_b$ and R$_c$ are each independently selected from C$_1$–C$_{12}$ alkyl, aryl, or substituted aryl; or
R$_2$' and R$_4$'' are as defined in claim 1; with

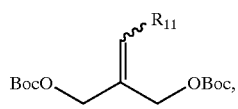

wherein R$_{11}$ is as defined in claim 1, in the presence of a phosphine ligand and Pd(O) catalyst under reflux conditions to prepare a compound of the formula:

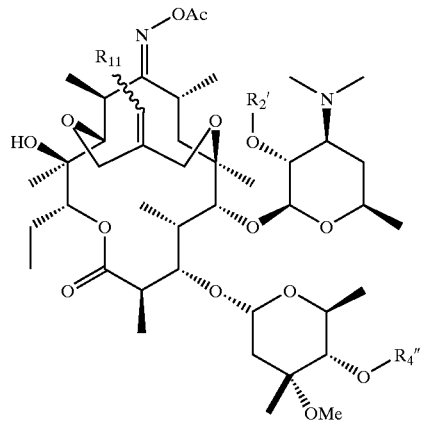

wherein R$_{11}$, R$_2$', and R$_4$'' are as defined in claim 1;
  (2) reacting the compound prepared in step (1) with a mild acid to prepare a compound of the formula:

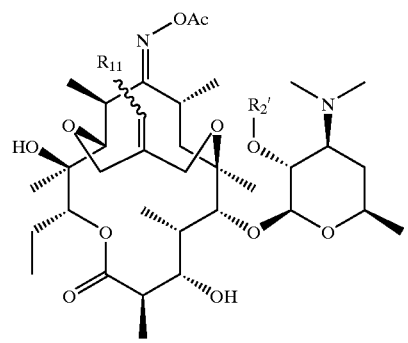

wherein R$_{11}$ and R$_2$' are as defined in claim 1;
  (3) reacting the compound prepared in step (2) with an oxime activating agent and quenching with methanol to prepare a compound of the formula:

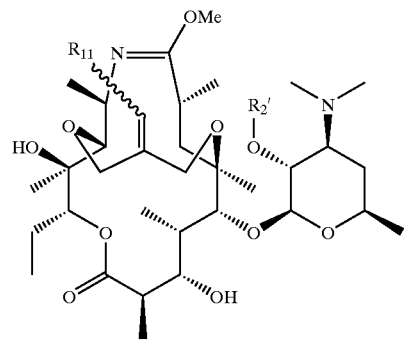

wherein R$_{11}$ and R$_2$' are as defined claim 1;
  (4) reacting the compound prepared in step (3) with a reducing agent to prepare compound of the formula:

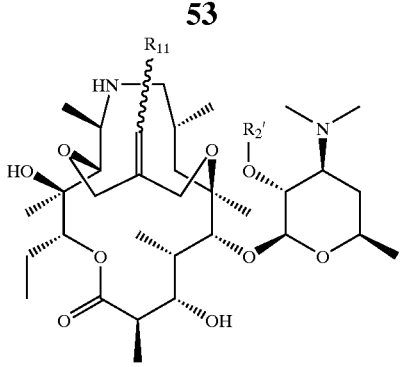

wherein R$_{11}$ and R$_2$' are as defined claim 1;

(5) reacting the compound prepared in step (4) with an alkylating agent, an alykyl halide in the presence of a base, or an aldehyde via reductive amination in the presence of NaCNBH$_3$ to prepare a compound of the formula:

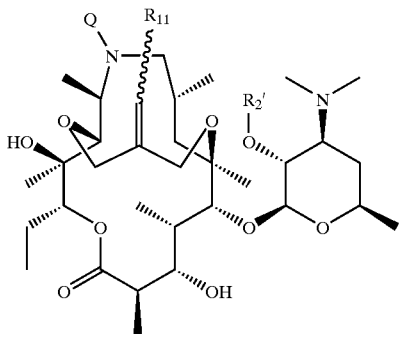

wherein Q, R$_{11}$, and R$_2$' is as defined claim 1; and (6) oxidizing the hydroxyl in the 3 position of the compound prepared in step (5) via Dess-Martin oxidation, Corey-Kim oxidation, or a Moffat oxidation to prepare a compound of the formula:

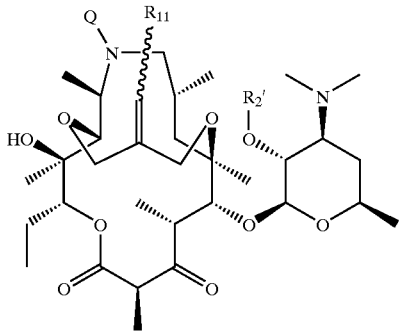

wherein Q, R$_{11}$, and R$_2$' are as defined claim 1.

11. A process of preparing compounds of the formula:

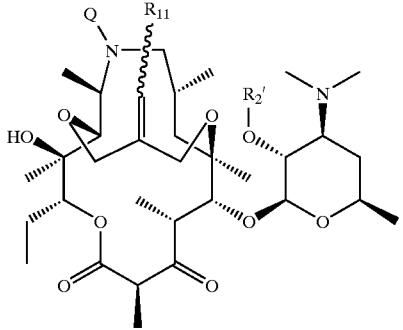

wherein Q, R$_2$', and R$_{11}$ are as defined in claim 1 comprising the step of reacting a compound of the formula:

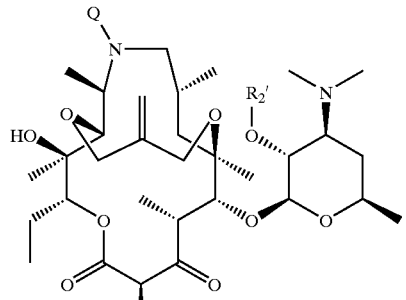

wherein Q and R$_2$' is as defined claim 1, with an aryl, alkenyl, or benzyl halide in the presence of an acceptable Heck reaction using a palladium catalyst and optionally with a phosphine ligand.

12. A process of preparing a compound of the formula:

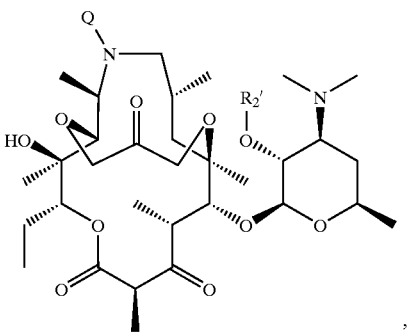

wherein Q and R$_2$' are as defined in claim 1, comprising the step of:

(a) performing ozonolysis on a compound of the formula:

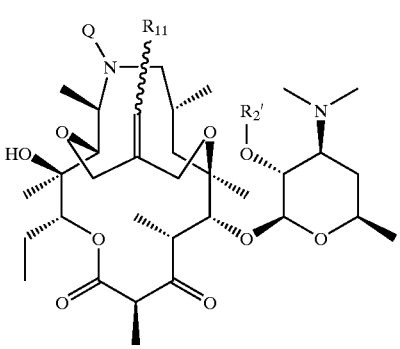

wherein Q and R$_2$' are as defined claim 1, and wherein R$_{11}$ is hydrogen.

13. A process of preparing a compound of the formula:

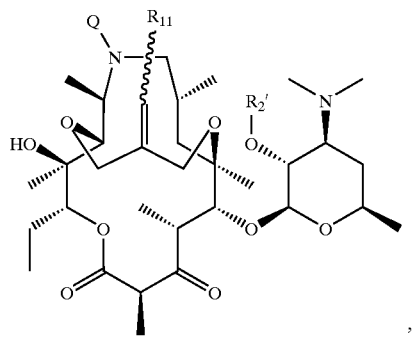

wherein Q, $R_2'$, and $R_{11}$ are as defined in claim 1, comprising the step of:

(a) reacting a compound of the formula:

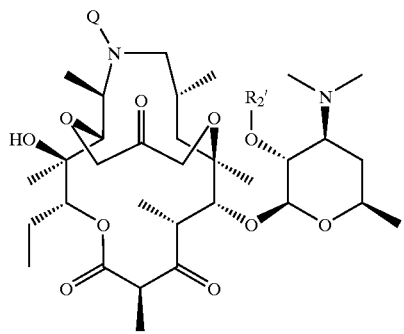

wherein Q and $R_2'$ are as defined in claim 1, with a phosphoylid under Wittig coitions.

14. A process of preparing a compound of the formula:

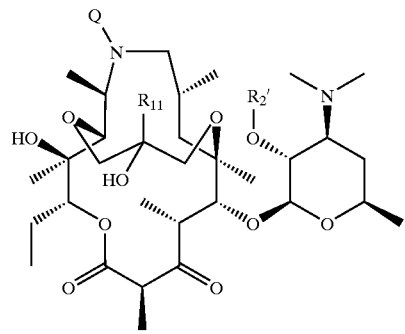

wherein Q, $R_2'$, and $R_{11}$ are as defined in claim 1, comprising the step of:

(a) reacting a compound of the formula:

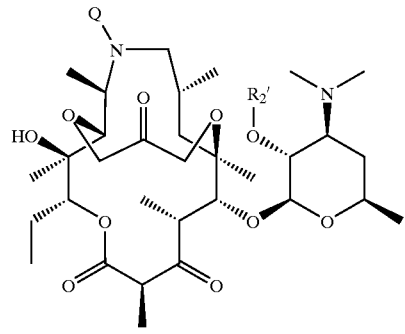

wherein Q and $R_2'$ are as defined in claim 1, with a Grignard reagent.

* * * * *